(12) United States Patent
Lee-Sepsick et al.

(10) Patent No.: US 11,154,326 B2
(45) Date of Patent: *Oct. 26, 2021

(54) METHODS AND DEVICES FOR SONOGRAPHIC IMAGING

(71) Applicant: Femasys, Inc., Suwanee, GA (US)

(72) Inventors: Kathy Lee-Sepsick, Suwanee, GA (US); Max S. Azevedo, Suwanee, GA (US)

(73) Assignee: FEMASYS INC., Suwanee, GA (US)

( * ) Notice: Subject to any disclaimer, the term of this patent is extended or adjusted under 35 U.S.C. 154(b) by 338 days.

This patent is subject to a terminal disclaimer.

(21) Appl. No.: 16/283,091

(22) Filed: Feb. 22, 2019

(65) Prior Publication Data

US 2019/0183529 A1 Jun. 20, 2019

Related U.S. Application Data

(63) Continuation of application No. 16/043,996, filed on Jul. 24, 2018, now Pat. No. 10,258,375, which is a continuation of application No. 12/245,265, filed on Oct. 3, 2008, now Pat. No. 10,070,888.

(51) Int. Cl.

| | |
|---|---|
| *A61B 8/14* | (2006.01) |
| *A61B 17/42* | (2006.01) |
| *A61M 5/00* | (2006.01) |
| *A61M 5/14* | (2006.01) |
| *A61M 25/10* | (2013.01) |
| *A61M 25/04* | (2006.01) |

(52) U.S. Cl.
CPC ............. *A61B 17/42* (2013.01); *A61M 5/007* (2013.01); *A61M 5/1407* (2013.01); *A61M 25/10* (2013.01); *A61M 25/04* (2013.01)

(58) Field of Classification Search
CPC ....... A61B 17/42; A61M 25/04; A61M 25/10; A61M 5/007; A61M 5/1407
See application file for complete search history.

(56) References Cited

U.S. PATENT DOCUMENTS

| | | | |
|---|---|---|---|
| 1,892,803 | A | 1/1933 | Lawshe |
| 3,042,030 | A | 7/1962 | Read |
| 3,182,662 | A | 5/1965 | Shirodkar |
| 3,404,682 | A | 10/1968 | Waldron |

(Continued)

FOREIGN PATENT DOCUMENTS

| | | |
|---|---|---|
| BR | 1120130114347 | 11/2011 |
| CA | 2556747 | 2/2005 |

(Continued)

OTHER PUBLICATIONS

Notice of Allowance dated Dec. 8, 2015 for U.S. Appl. No. 14/705,390, filed May 6, 2015 (Lee-Sepsick et al.—inventors) (8 pages).

(Continued)

*Primary Examiner* — Christopher L Cook
(74) *Attorney, Agent, or Firm* — Mary Anthony Merchant

(57) ABSTRACT

The present invention comprises methods and devices for providing contrast medium for sonography of structures such as ducts and cavities. The invention provides for creation of detectable acoustic variations between two generated phases of a gas and a liquid to make a contrast medium. Sonography is the primary means of imaging but other conventional detection means may also be employed with the present invention.

18 Claims, 5 Drawing Sheets

(56) References Cited

U.S. PATENT DOCUMENTS

| | | |
|---|---|---|
| 3,405,711 A | 10/1968 | Bakunin |
| 3,422,813 A | 1/1969 | Braley et al. |
| 3,463,141 A | 8/1969 | Mozolf |
| 3,467,090 A | 9/1969 | Zollett |
| 3,598,115 A | 8/1971 | Home |
| 3,645,258 A | 2/1972 | Massouras |
| 3,675,642 A | 7/1972 | Lord |
| 3,680,542 A | 8/1972 | Cimber |
| 3,687,129 A | 8/1972 | Nuwayser |
| 3,768,102 A | 10/1973 | Kwan-Gett et al. |
| 3,774,600 A | 11/1973 | Cognat |
| 3,803,308 A | 4/1974 | Zipper |
| 3,805,767 A | 4/1974 | Erb |
| 3,822,702 A | 7/1974 | Bolduc et al. |
| 3,855,996 A | 12/1974 | Bolduc |
| 3,856,016 A | 12/1974 | Davis |
| 3,858,571 A | 1/1975 | Rudolph |
| 3,858,586 A | 1/1975 | Lessen |
| 3,871,374 A | 3/1975 | Bolduc et al. |
| 3,875,939 A | 4/1975 | Bolduc et al. |
| 3,882,854 A | 5/1975 | Hulka et al. |
| 3,918,431 A | 11/1975 | Sinnreich |
| 3,948,259 A | 4/1976 | Bolduc et al. |
| 3,954,108 A | 5/1976 | Davis |
| 3,967,625 A | 7/1976 | Yoon |
| 3,972,331 A | 8/1976 | Bolduc et al. |
| 3,973,560 A | 8/1976 | Emmett |
| RE29,207 E | 5/1977 | Bolduc et al. |
| RE29,345 E | 8/1977 | Erb |
| 4,109,654 A | 8/1978 | Bolduc et al. |
| 4,119,098 A | 10/1978 | Bolduc et al. |
| 4,126,134 A | 11/1978 | Bolduc et al. |
| 4,135,495 A | 1/1979 | Borgen |
| 4,136,695 A | 1/1979 | Dafoe |
| 4,158,050 A | 6/1979 | Zipper |
| 4,160,446 A | 7/1979 | Barrington |
| 4,181,725 A | 1/1980 | Voorhees et al. |
| 4,182,328 A | 1/1980 | Bolduc et al. |
| 4,185,618 A | 1/1980 | Corey |
| 4,207,891 A | 6/1980 | Bolduc |
| 4,226,239 A | 10/1980 | Polk et al. |
| 4,230,116 A | 10/1980 | Watson |
| 4,245,623 A | 1/1981 | Erb |
| 4,267,839 A | 5/1981 | Laufe et al. |
| 4,359,454 A | 11/1982 | Hoffman |
| 4,365,621 A | 12/1982 | Brundin |
| 4,374,523 A | 2/1983 | Yoon |
| 4,380,238 A | 4/1983 | Colucci et al. |
| 4,416,660 A | 11/1983 | Dafoe |
| 4,466,442 A | 8/1984 | Hilmann et al. |
| 4,485,814 A | 12/1984 | Yoon |
| 4,489,725 A | 12/1984 | Casey et al. |
| 4,509,504 A | 4/1985 | Brundin |
| 4,523,590 A | 6/1985 | Roth et al. |
| 4,537,186 A | 8/1985 | Verschoof et al. |
| 4,547,188 A | 10/1985 | Bolduc |
| 4,548,201 A | 10/1985 | Yoon |
| 4,579,110 A | 4/1986 | Hamou |
| 4,595,000 A | 6/1986 | Hamou |
| 4,601,698 A | 7/1986 | Moulding, Jr. |
| 4,606,336 A | 8/1986 | Zeluff |
| 4,611,602 A | 9/1986 | Bolduc |
| 4,631,188 A | 12/1986 | Stoy et al. |
| 4,637,818 A | 1/1987 | Johnson et al. |
| 4,664,112 A | 5/1987 | Kensey et al. |
| 4,679,558 A | 7/1987 | Kensey et al. |
| 4,681,106 A | 7/1987 | Kensey et al. |
| 4,700,701 A | 10/1987 | Montaldi |
| 4,700,705 A | 10/1987 | Kensey et al. |
| 4,713,235 A | 12/1987 | Krall |
| 4,731,052 A | 3/1988 | Seitz, Jr. |
| 4,788,966 A | 12/1988 | Yoon |
| 4,794,927 A | 1/1989 | Yoon |
| 4,795,438 A | 1/1989 | Kensey et al. |
| 4,804,691 A | 2/1989 | English et al. |
| 4,808,399 A | 2/1989 | Rypacek et al. |
| 4,824,434 A | 4/1989 | Seitz, Jr. |
| 4,832,941 A | 5/1989 | Berwing et al. |
| 4,834,091 A | 5/1989 | Ott |
| 4,847,065 A | 7/1989 | Akimova et al. |
| 4,869,268 A | 9/1989 | Yoon |
| 4,932,422 A | 6/1990 | Ragheb |
| 4,937,254 A | 6/1990 | Sheffield et al. |
| 4,938,763 A | 7/1990 | Dunn et al. |
| 4,983,177 A | 1/1991 | Wolf |
| 5,026,379 A | 6/1991 | Yoon |
| 5,065,751 A | 11/1991 | Wolf |
| 5,095,917 A | 3/1992 | Vancaillie |
| 5,147,353 A | 9/1992 | Everett |
| 5,193,554 A | 3/1993 | McQuilkin |
| 5,211,627 A | 5/1993 | William |
| 5,217,030 A | 6/1993 | Yoon |
| 5,217,473 A | 6/1993 | Yoon |
| 5,226,908 A | 7/1993 | Yoon |
| 5,273,527 A | 12/1993 | Schatz et al. |
| 5,278,201 A | 1/1994 | Dunn et al. |
| 5,278,202 A | 1/1994 | Dunn et al. |
| 5,324,519 A | 6/1994 | Dunn et al. |
| 5,328,687 A | 7/1994 | Leung et al. |
| 5,334,209 A | 8/1994 | Yoon |
| 5,340,849 A | 8/1994 | Dunn et al. |
| 5,350,798 A | 9/1994 | Linden et al. |
| 5,352,436 A | 10/1994 | Wheatley et al. |
| 5,364,345 A | 11/1994 | Lowery et al. |
| 5,372,584 A | 12/1994 | Zink et al. |
| 5,374,247 A | 12/1994 | Lowery et al. |
| 5,389,089 A | 2/1995 | Bauer et al. |
| 5,391,146 A | 2/1995 | That et al. |
| 5,464,395 A | 11/1995 | Faxon et al. |
| 5,469,867 A | 11/1995 | Schmitt |
| 5,474,089 A | 12/1995 | Waynant |
| 5,478,837 A | 12/1995 | Rodgers et al. |
| 5,487,390 A | 1/1996 | Cohen et al. |
| 5,487,897 A | 1/1996 | Poison et al. |
| 5,551,443 A | 9/1996 | Sepetka et al. |
| 5,562,099 A | 10/1996 | Cohen et al. |
| 5,575,802 A | 11/1996 | McQuilkin et al. |
| 5,599,552 A | 2/1997 | Dunn et al. |
| 5,601,600 A | 2/1997 | Ton |
| 5,612,052 A | 3/1997 | Shalaby |
| 5,632,727 A | 5/1997 | Tipton et al. |
| 5,632,753 A | 5/1997 | Loeser |
| 5,634,877 A | 6/1997 | Salama |
| 5,681,873 A | 10/1997 | Norton et al. |
| 5,701,899 A | 12/1997 | Porter |
| 5,702,716 A | 12/1997 | Dunn et al. |
| 5,702,717 A | 12/1997 | Cha et al. |
| 5,704,899 A | 1/1998 | Milo |
| 5,714,159 A | 2/1998 | Shalaby |
| 5,716,321 A | 2/1998 | Kerin et al. |
| 5,725,777 A | 3/1998 | Taylor |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,780,044 A | 4/1998 | Yewey et al. |
| 5,746,769 A | 5/1998 | Ton et al. |
| 5,747,058 A | 5/1998 | Tipton et al. |
| 5,752,974 A | 5/1998 | Rhee et al. |
| 5,759,563 A | 6/1998 | Yewey et al. |
| 5,788,716 A | 8/1998 | Kobren et al. |
| 5,792,469 A | 8/1998 | Tipton et al. |
| 5,795,288 A | 8/1998 | Cohen et al. |
| 5,795,331 A | 8/1998 | Cragg et al. |
| 5,807,239 A | 9/1998 | DiBernardo |
| 5,826,584 A | 10/1998 | Schmitt |
| 5,830,228 A | 11/1998 | Knapp et al. |
| 5,843,121 A | 12/1998 | Yoon |
| 5,846,255 A | 12/1998 | Casey |
| 5,866,554 A | 2/1999 | Shalaby et al. |
| 5,873,815 A | 2/1999 | Kerin et al. |
| 5,885,601 A | 3/1999 | Sokal |
| 5,888,533 A | 3/1999 | Dunn |
| 5,891,192 A | 4/1999 | Murayama et al. |

(56) References Cited

U.S. PATENT DOCUMENTS

| | | |
|---|---|---|
| 5,891,457 A | 4/1999 | Neuwirth |
| 5,894,022 A | 4/1999 | Ji et al. |
| 5,919,434 A | 7/1999 | Dugstad et al. |
| 5,935,056 A | 8/1999 | Kerin et al. |
| 5,935,098 A | 8/1999 | Blaisdell et al. |
| 5,935,137 A | 8/1999 | Saadat et al. |
| 5,947,958 A | 9/1999 | Woodard et al. |
| 5,947,977 A | 9/1999 | Slepian et al. |
| 5,954,715 A | 9/1999 | Harrington et al. |
| 5,955,143 A | 9/1999 | Wheatley et al. |
| 5,962,006 A | 10/1999 | Southard et al. |
| 5,968,542 A | 10/1999 | Tipton |
| 5,972,002 A | 10/1999 | Bark et al. |
| 5,979,446 A | 11/1999 | Loy |
| 5,989,580 A | 11/1999 | Wallace et al. |
| 5,990,194 A | 11/1999 | Dunn et al. |
| 6,010,714 A | 1/2000 | Leung et al. |
| 6,019,757 A | 2/2000 | Scheldrup |
| 6,026,331 A | 2/2000 | Feldberg et al. |
| 6,037,331 A | 3/2000 | Shalaby et al. |
| 6,042,590 A | 3/2000 | Sporri et al. |
| 6,066,139 A | 5/2000 | Ryan et al. |
| 6,068,626 A | 5/2000 | Harrington et al. |
| 6,071,283 A | 6/2000 | Nardella et al. |
| 6,080,129 A | 6/2000 | Blaisdell |
| 6,080,152 A | 6/2000 | Nardella et al. |
| 6,096,052 A | 8/2000 | Callister et al. |
| 6,103,254 A | 8/2000 | Wallace et al. |
| 6,112,747 A | 9/2000 | Jones et al. |
| 6,113,614 A | 9/2000 | Mears |
| 6,120,789 A | 9/2000 | Dunn |
| 6,130,200 A | 10/2000 | Brodbeck et al. |
| 6,143,352 A | 11/2000 | Clark et al. |
| 6,145,505 A | 11/2000 | Nikolchev et al. |
| 6,152,943 A | 11/2000 | Sawhney |
| 6,165,492 A | 12/2000 | Neuwirth |
| 6,174,919 B1 | 1/2001 | Hickey |
| 6,176,240 B1 | 1/2001 | Nikolchev et al. |
| 6,179,832 B1 | 1/2001 | Jones et al. |
| 6,187,346 B1 | 2/2001 | Neuwirth |
| 6,196,966 B1 | 3/2001 | Kerin et al. |
| 6,197,351 B1 | 3/2001 | Neuwirth |
| 6,245,090 B1 | 6/2001 | Gilson et al. |
| 6,258,084 B1 | 7/2001 | Goldman et al. |
| 6,297,337 B1 | 7/2001 | Marchant et al. |
| 6,290,672 B1 | 9/2001 | Abae |
| 6,299,631 B1 | 10/2001 | Shalaby |
| 6,306,243 B1 | 10/2001 | Clark et al. |
| 6,309,384 B1 | 10/2001 | Harrington et al. |
| 6,327,505 B1 | 12/2001 | Medhkour et al. |
| 6,346,102 B1 | 2/2002 | Harrington et al. |
| 6,357,443 B1 | 3/2002 | Loy |
| 6,371,975 B2 | 4/2002 | Cruise et al. |
| 6,378,524 B1 | 4/2002 | Jones |
| 6,379,373 B1 | 4/2002 | Sawhney et al. |
| 6,395,293 B2 | 5/2002 | Poison et al. |
| 6,401,719 B1 | 6/2002 | Farley et al. |
| 6,413,536 B1 | 7/2002 | Gibson et al. |
| 6,413,539 B1 | 7/2002 | Shalaby |
| 6,432,116 B1 | 8/2002 | Callister et al. |
| 6,433,096 B1 | 8/2002 | Hickey et al. |
| 6,450,963 B1 | 9/2002 | Ackerman |
| 6,455,064 B1 | 9/2002 | Narang et al. |
| 6,458,147 B1 | 10/2002 | Cruise et al. |
| 6,461,631 B1 | 10/2002 | Dunn et al. |
| 6,465,001 B1 | 10/2002 | Hubbell et al. |
| 6,493,589 B1 | 10/2002 | Medhkour et al. |
| 6,476,069 B2 | 11/2002 | Krall et al. |
| 6,476,070 B2 | 11/2002 | Krall et al. |
| 6,485,486 B1 | 11/2002 | Trembly et al. |
| RE37,950 E | 12/2002 | Dunn et al. |
| 6,514,534 B1 | 2/2003 | Sawhney |
| 6,514,535 B2 | 2/2003 | Marchant |
| 6,526,979 B1 | 3/2003 | Nikolchev et al. |
| 6,528,080 B2 | 3/2003 | Dunn et al. |
| 6,538,026 B1 | 3/2003 | Krall et al. |
| 6,539,265 B2 | 3/2003 | Medhkour et al. |
| 6,550,480 B2 | 4/2003 | Feldman et al. |
| 6,565,557 B1 | 5/2003 | Sporri et al. |
| 6,577,903 B1 | 6/2003 | Cronin et al. |
| 6,579,469 B1 | 6/2003 | Nicholson et al. |
| 6,599,299 B2 | 7/2003 | Schultz |
| 6,605,294 B2 | 8/2003 | Sawhney |
| 6,605,667 B1 | 8/2003 | Badejo et al. |
| 6,607,631 B1 | 8/2003 | Badejo et al. |
| 6,610,033 B1 | 8/2003 | Melanson et al. |
| 6,620,846 B1 | 9/2003 | Jonn et al. |
| 6,634,361 B1 | 10/2003 | Nikolchev et al. |
| 6,635,055 B1 | 10/2003 | Cronin |
| 6,663,607 B2 | 12/2003 | Slaikeu et al. |
| 6,676,971 B2 | 1/2004 | Goupil et al. |
| 6,679,266 B2 | 1/2004 | Nikolchev et al. |
| 6,682,526 B1 | 1/2004 | Jones et al. |
| 6,684,884 B2 | 2/2004 | Nikolchev et al. |
| 6,689,148 B2 | 2/2004 | Sawhney et al. |
| 6,699,940 B2 | 3/2004 | Shalaby |
| 6,703,047 B2 | 3/2004 | Sawhney et al. |
| 6,705,323 B1 | 3/2004 | Nikolchev et al. |
| 6,709,667 B1 | 3/2004 | Lowe et al. |
| 6,712,810 B2 | 3/2004 | Harrington et al. |
| 6,723,144 B2 | 4/2004 | Katagiri et al. |
| 6,723,781 B1 | 4/2004 | Frate et al. |
| 6,726,682 B2 | 4/2004 | Harrington et al. |
| 6,736,822 B2 | 5/2004 | McClellan et al. |
| 6,743,248 B2 | 6/2004 | Edwards et al. |
| 6,752,803 B2 | 6/2004 | Goldman et al. |
| 6,758,831 B2 | 7/2004 | Ryan |
| 6,763,833 B1 | 7/2004 | Khera et al. |
| 6,780,182 B2 | 8/2004 | Bowman et al. |
| 8,048,086 B2 | 11/2011 | Lee-Sepsick et al. |
| 8,048,101 B2 | 11/2011 | Lee-Sepsick et al. |
| 8,052,669 B2 | 11/2011 | Lee-Sepsick et al. |
| 8,695,606 B2 | 4/2014 | Lee-Sepsick |
| 8,726,906 B2 | 5/2014 | Lee-Sepsick |
| 9,034,053 B2 | 5/2015 | Lee-Sepsick |
| 9,220,880 B2 | 12/2015 | Lee-Sepsick |
| 9,308,023 B2 | 4/2016 | Lee-Sepsick |
| 9,402,762 B2 | 8/2016 | Lee-Sepsick |
| 9,554,826 B2 | 1/2017 | Lee-Sepsick |
| 9,838,444 B2 | 12/2017 | Ip et al. |
| 10,111,687 B2 | 10/2018 | Lee-Sepsick |
| 10,172,643 B2 | 1/2019 | Lee-Sepsick |
| 10,258,375 B2 | 4/2019 | Lee-Sepsick |
| 10,292,732 B2 | 5/2019 | Lee-Sepsick |
| 2001/0001673 A1 | 8/2001 | Harrington et al. |
| 2001/0016738 A1 | 8/2001 | Harrington et al. |
| 2001/0016739 A1 | 8/2001 | Goldman et al. |
| 2001/0023365 A1 | 9/2001 | Medhkour et al. |
| 2001/0041900 A1 | 11/2001 | Callister et al. |
| 2002/0013589 A1 | 1/2002 | Callister et al. |
| 2002/0020417 A1 | 2/2002 | Nikolchev et al. |
| 2002/0029051 A1 | 3/2002 | Callister et al. |
| 2002/0035101 A1 | 3/2002 | Dey et al. |
| 2002/0072744 A1 | 5/2002 | Harrington et al. |
| 2002/0082636 A1 | 6/2002 | Sawhney et al. |
| 2002/0095082 A1 | 7/2002 | Evans et al. |
| 2002/0106411 A1 | 8/2002 | Wironen et al. |
| 2002/0133140 A1 | 9/2002 | Moulis |
| 2002/0148476 A1 | 10/2002 | Farley et al. |
| 2002/0176893 A1 | 11/2002 | Wironen et al. |
| 2002/0177846 A1 | 11/2002 | Mulier et al. |
| 2002/0177855 A1 | 11/2002 | Greene, Jr. et al. |
| 2003/0015203 A1 | 1/2003 | Makower et al. |
| 2003/0029457 A1 | 2/2003 | Callister et al. |
| 2003/0005173 A1 | 3/2003 | Pavcnik et al. |
| 2003/0051735 A1 | 3/2003 | Pavcnik et al. |
| 2003/0060800 A1 | 3/2003 | Ryan |
| 2003/0066533 A1 | 4/2003 | Loy |
| 2003/0082636 A1 | 5/2003 | Wong |
| 2003/0108586 A1 | 6/2003 | Ramey |
| 2003/0134032 A1 | 7/2003 | Chaouk et al. |
| 2003/0158563 A1 | 8/2003 | McClellan et al. |
| 2003/0170173 A1 | 9/2003 | Klaveness et al. |
| 2003/0171759 A1 | 9/2003 | Sadler et al. |

(56) References Cited

U.S. PATENT DOCUMENTS

| | | |
|---|---|---|
| 2003/0185896 A1 | 10/2003 | Buiser et al. |
| 2003/0194389 A1 | 10/2003 | Porter |
| 2003/0194390 A1 | 10/2003 | Krall et al. |
| 2003/0223956 A1 | 12/2003 | Goupil et al. |
| 2004/0002680 A1 | 1/2004 | Ackerman et al. |
| 2004/0010229 A1 | 1/2004 | Houde |
| 2004/0000793 A1 | 4/2004 | Nikolchev et al. |
| 2004/0079377 A1 | 4/2004 | Nikolchev et al. |
| 2004/0127918 A1 | 7/2004 | Nikolchev et al. |
| 2004/0001613 A1 | 8/2004 | Wheatley et al. |
| 2004/0159324 A1 | 8/2004 | Nikolchev et al. |
| 2004/0161384 A1 | 8/2004 | Wheatley et al. |
| 2004/0163650 A1 | 8/2004 | Lowe et al. |
| 2004/0002063 A1 | 10/2004 | Nikolchev et al. |
| 2004/0204720 A1 | 10/2004 | Harrington et al. |
| 2004/0206358 A1 | 10/2004 | Nikolchev et al. |
| 2004/0211429 A1 | 10/2004 | Nikolchev et al. |
| 2004/0215215 A1 | 10/2004 | McClellan et al. |
| 2004/0241874 A1 | 12/2004 | Abdel-Rehim |
| 2004/0258761 A1 | 12/2004 | Wheatley et al. |
| 2004/0258769 A1 | 12/2004 | Barker et al. |
| 2005/0187561 A1 | 8/2005 | Lee-Sepsick et al. |
| 2005/0240211 A1 | 10/2005 | Sporri et al. |
| 2006/0100511 A1 | 5/2006 | Eriksen |
| 2006/0178620 A1 | 8/2006 | Wollmann et al. |
| 2007/0197963 A1 | 8/2007 | Griffiths et al. |
| 2008/0058720 A1 | 3/2008 | Spohn |
| 2008/0063603 A1 | 3/2008 | Schneider et al. |
| 2008/0264865 A1 | 10/2008 | Herman |
| 2008/0312636 A1 | 12/2008 | Miller |
| 2009/0002415 A1 | 1/2009 | Lee-Sepsick et al. |
| 2009/0024108 A1 | 1/2009 | Lee-Sepsick et al. |
| 2009/0217932 A1 | 9/2009 | Voegele |
| 2009/0277455 A1 | 11/2009 | Lee-Sepsick et al. |
| 2009/0306623 A1 | 12/2009 | McIntosh et al. |
| 2010/0086492 A1 | 4/2010 | Lee-Sepsick et al. |
| 2011/0137150 A1 | 6/2011 | Connor et al. |
| 2012/0035471 A1 | 2/2012 | Lee-Sepsick et al. |
| 2012/0042879 A1 | 2/2012 | Lee-Sepsick et al. |
| 2012/0042880 A1 | 2/2012 | Lee-Sepsick et al. |
| 2012/0046260 A1 | 2/2012 | Lee-Sepsick et al. |
| 2019/0076169 A1 | 3/2019 | Lee-Sepsick et al. |
| 2019/0282270 A1 | 9/2019 | Lee-Sepsick et al. |

FOREIGN PATENT DOCUMENTS

| | | |
|---|---|---|
| CA | 2817296 | 11/2011 |
| CH | 2367591 | 10/2009 |
| CN | 200580006068.X | 2/2005 |
| CN | 201110353992.2 | 11/2011 |
| CN | 201810335624.7 | 11/2011 |
| DE | 2537620 | 2/1977 |
| DE | 3324754 | 7/1983 |
| DE | 1722732 | 5/2005 |
| DE | 602009052878.50 | 10/2009 |
| EP | 05723981.6 | 2/2005 |
| EP | 2367591 | 10/2009 |
| EP | 09793278.4 | 10/2009 |
| EP | 11839530.0 | 11/2011 |
| FR | 2414925 | 8/1979 |
| FR | 1722732 | 5/2005 |
| FR | 2367591 | 10/2009 |
| GB | 1470571 | 4/1977 |
| GB | 1722732 | 5/2005 |
| GB | 2367591 | 10/2009 |
| HK | 07105332.9 | 2/2005 |
| HK | 1098042 | 5/2005 |
| HK | 1162367 | 10/2009 |
| HK | 18114378.3 | 11/2011 |
| IE | 1722732 | 5/2005 |
| IE | 2367591 | 10/2009 |
| IN | 2536/KOLNP/06 | 2/2005 |
| IN | 5058DELNP/2013 | 11/2011 |
| JP | 59-046500 | 3/1984 |
| JP | 2002-200176 | 7/2002 |
| JP | 2007-500782 | 2/2005 |
| JP | 2011-245163 | 11/2011 |
| JP | 6012159 | 11/2011 |
| KR | 1973797 | 11/2011 |
| WO | WO 1981/000701 | 3/1981 |
| WO | WO 1988/009648 | 12/1988 |
| WO | WO 1993/014786 | 8/1993 |
| WO | WO 1994/024944 | 11/1994 |
| WO | WO 1994/028803 | 12/1994 |
| WO | WO 1995/019184 | 7/1995 |
| WO | WO 1995/025490 | 9/1995 |
| WO | WO 1997/012569 | 4/1997 |
| WO | WO 1997/042987 | 11/1997 |
| WO | WO 1997/049345 | 12/1997 |
| WO | WO 1998/026737 | 6/1998 |
| WO | WO 1998/031308 | 7/1998 |
| WO | WO 1999/007297 | 2/1999 |
| WO | WO 1999/047073 | 9/1999 |
| WO | WO 2000/018469 | 4/2000 |
| WO | WO 2000/024374 | 5/2000 |
| WO | WO 2000/044323 | 8/2000 |
| WO | WO 2000/054746 | 9/2000 |
| WO | WO 2001/037760 | 5/2001 |
| WO | WO 2002/039880 | 5/2002 |
| WO | WO 2002/047744 | 6/2002 |
| WO | WO 2003/070085 | 3/2003 |
| WO | WO 2004/024237 | 3/2004 |
| WO | WO 2004/035022 | 4/2004 |
| WO | PCT/US2005/006334 | 2/2005 |
| WO | WO 2005/082299 | 9/2005 |
| WO | PCT/US2009/059370 | 10/2009 |
| WO | WO 2010/040046 | 4/2010 |
| WO | PCT/US2011/06013 | 11/2011 |

OTHER PUBLICATIONS

Approval of Terminal Disclaimer issued Nov. 2, 2015 for U.S. Appl. No. 14/705,390, filed May 6, 2015 (Lee-Sepsick et al.—inventors) (4 pages).

Response to Non-Final Office Action dated Oct. 17, 2015 for U.S. Appl. No. 14/705,390, filed May 6, 2015 (Lee-Sepsick et al.—inventors) (8 pages).

Non-Final Office Action dated Jul. 17, 2015 for U.S. Appl. No. 14/705,390, filed May 6, 2015 (Lee-Sepsick et al.—inventors) (8 pages).

Issue Notification dated Nov. 21, 2017 for U.S. Appl. No. 15/082,912, filed Apr. 4, 2016 (Lee-Sepsick et al.—inventors) (1 page).

Corrected Notice of Allowance dated Nov. 17, 2017 for U.S. Appl. No. 15/082,912, filed Apr. 4, 2016 (Lee-Sepsick et al.—inventors) (4 pages).

Notice of Allowance issued Aug. 3, 2017 for U.S. Appl. No. 15/082,912, filed Apr. 4, 2016 (Lee-Sepsick et al.—inventors) (8 pages).

Response to Final Office Action dated Jul. 13, 2017 for U.S. Appl. No. 15/082,912, filed Apr. 4, 2016 (Lee-Sepsick et al.—inventors) (13 pages).

Final Office Action dated Apr. 21, 2017 for U.S. Appl. No. 15/082,912, filed Apr. 4, 2016 (Lee-Sepsick et al.—inventors) (29 pages).

Response to Non-Final Office Action dated Feb. 121, 2017 for U.S. Appl. No. 15/082,912, filed Apr. 4, 2016 (Lee-Sepsick et al.—inventors) (9 pages).

Non-Final Office Action dated Nov. 18, 2016 for U.S. Appl. No. 15/082,912, filed Apr. 4, 2016 (Lee-Sepsick et al.—inventors) (29 pages).

Non-Final Office Action dated Mar. 16, 2018 for U.S. Appl. No. 15/793,306, filed Oct. 25, 2017 (Lee-Sepsick et al.—inventors) (28 pages).

Issue Notification dated Jan. 11, 2017 for U.S. Appl. No. 13/219,867, filed Aug. 27, 2011 (Lee-Sepsick et al.—inventors) (1 page).

Response to 312 Amendment dated Nov. 2, 2016 for U.S. Appl. No. 13/219,867, filed Aug. 27, 2011 (Lee-Sepsick et al.—inventors) (2 pages).

312 Amendment dated Oct. 27, 2016 for U.S. Appl. No. 13/219,867, filed Aug. 27, 2011 (Lee-Sepsick et al.—inventors) (4 pages).

(56) References Cited

OTHER PUBLICATIONS

Notice of Allowance dated Sep. 19, 2016 for U.S. Appl. No. 13/219,867, filed Aug. 27, 2011 (Lee-Sepsick et al.—inventors) (10 pages).
Response to Final Office Action dated Sep. 2, 2016 for U.S. Appl. No. 13/219,867, filed Aug. 27, 2011 (Lee-Sepsick et al.—inventors) (17 pages).
Final Office Action dated Jun. 9, 2016 for U.S. Appl. No. 13/219,867, filed Aug. 27, 2011 (Lee-Sepsick et al.—inventors) (20 pages).
Response to Non-Final Office Action dated Mar. 10, 2016 for U.S. Appl. No. 13/219,867, filed Aug. 27, 2011 (Lee-Sepsick et al.—inventors) (10 pages).
Non-Final Office Action dated Sep. 10, 2015 for U.S. Appl. No. 13/219,867, filed Aug. 27, 2011 (Lee-Sepsick et al.—inventors) (11 pages).
Request for Continued Examination dated Mar. 3, 2015 for U.S. Appl. No. 13/219,867, filed Aug. 27, 2011 (Lee-Sepsick et al.—inventors) (10 pages).
Final Office Action dated Sep. 3, 2014 for U.S. Appl. No. 13/219,867, filed Aug. 27, 2011 (Lee-Sepsick et al.—inventors) (10 pages).
Response to Non-Final Office Action dated Aug. 8, 2014 for U.S. Appl. No. 13/219,867, filed Aug. 27, 2011 (Lee-Sepsick et al.—inventors) (10 pages).
Non-Final Office Action dated May 8, 2014 for U.S. Appl. No. 13/219,867, filed Aug. 27, 2011 (Lee-Sepsick et al.—inventors) (12 pages).
Request for Continued Examination dated Feb. 19, 2018 for U.S. Appl. No. 13/219,867, filed Aug. 27, 2011 (Lee-Sepsick et al.—inventors) (11 pages).
Final Office Action dated Nov. 17, 2017 for U.S. Appl. No. 13/219,867, filed Aug. 27, 2011 (Lee-Sepsick et al.—inventors) (13 pages).
Preliminary Amendment dated May 25, 2017 for U.S. Appl. No. 13/219,867, filed Aug. 27, 2011 (Lee-Sepsick et al.—inventors) (7 pages).
Decision to Grant dated Feb. 28, 2013 for European Patent Application No. 05723981.3 which claims priority to PCT/US2005/006334 filed Feb. 25, 2005 (Lee-Sepsick et al.—inventors; Femasys, Inc.—Applicant) (2 Pages).
Examination Report dated Jun. 7, 2012 for Canadian Patent Application No. 2556747 which claims priority to PCT/US2005/006334 filed Feb. 25, 2005 (Lee-Sepsick et al.—inventors; Femasys, Inc.—Applicant) (2 Pages).
Response to Examination Report dated Oct. 12, 2012 for Canadian Patent Application No. 2556747 which claims priority to PCT/US2005/006334 filed Feb. 25, 2005 (Lee-Sepsick et al.—inventors; Femasys, Inc.—Applicant) (3 Pages).
Notice of Canadian Patent dated Jul. 30, 2013 for Canadian Patent Application No. 2556747 which claims priority to PCT/US2005/006334 filed Feb. 25, 2005 (Lee-Sepsick et al.—inventors; Femasys, Inc.—Applicant) (3 Pages).
Notice of Indian Patent dated Sep. 12, 2014 for Indian Patent Application No. 2536/KOLNP/06 which claims priority to PCT/US2005/006334 filed Feb. 25, 2005 (Lee-Sepsick et al.—inventors; Femasys, Inc.—Applicant) (2 Pages).
Request Examination dated Sep. 30, 204 for Canadian Patent Application No. 2770504 which claims priority to PCT/US2009/05937 filed Oct. 2, 2009 (Lee-Sepsick et al.—inventors; Femasys, Inc.—Applicant) (1 Page).
Examination Report dated Nov. 20, 2015 for Canadian Patent Application No. 2770504 which claims priority to PCT/US2009/05937 filed Oct. 2, 2009 (Lee-Sepsick et al.—inventors; Femasys, Inc.—Applicant) (3 Pages).
Response to Examination Report dated May 20, 2016 or Canadian Patent Application No. 2770504 which claims priority to PCT/US2009/05937 filed Oct. 2, 2009 (Lee-Sepsick et al.—inventors; Femasys, Inc.—Applicant) (12 Pages).
Examination Report dated Oct. 28, 2016 for Canadian Patent Application No. 2770504 which claims priority to PCT/US2009/05937 filed Oct. 2, 2009 (Lee-Sepsick et al.—inventors; Femasys, Inc.—Applicant) (3 Pages).
Response to Examination Report dated Apr. 25, 2017 for Canadian Patent Application No. 2770504 which claims priority to PCT/US2009/05937 filed Oct. 2, 2009 (Lee-Sepsick et al.—inventors; Femasys, Inc.—Applicant) (8 Pages).
Patent Grant Notice dated Mar. 6, 2018 for Canadian Patent Application No. 2770504 which claims priority to PCT/US2009/05937 filed Oct. 2, 2009 (Lee-Sepsick et al.—inventors; Femasys, Inc.—Applicant) (1 Page).
Examination Report dated May 24, 2017 for European Patent Application No. 09793278.4 which claims priority to PCT/US2009/05937 filed Oct. 2, 2009 (Lee-Sepsick et al.—inventors; Femasys, Inc.—Applicant) (4 Pages).
Response to Examination Report dated Sep. 29, 2017 for European Patent Application No. 09793278.4 which claims priority to PCT/US2009/05937 filed Oct. 2, 2009 (Lee-Sepsick et al.—inventors; Femasys, Inc.—Applicant) (6 Pages).
Intention to Grant dated Jan. 11, 2018 for European Patent Application No. 09793278.4 which claims priority to PCT/US2009/05937 filed Oct. 2, 2009 (Lee-Sepsick et al.—inventors; Femasys, Inc.—Applicant) (5 Pages).
Request for Examination dated Oct. 24, 2016 for Canadian Patent Application No. 2817296 which claims priority to PCT/US2011/060013 filed Nov. 9, 2011 (Lee-Sepsick et al.—inventors; Femasys, Inc.—Applicant) (1 Page).
Examination Report dated Aug. 9, 2017 for Canadian Patent Application No. 2817296 which claims priority to PCT/US2011/060013 filed Nov. 9, 2011 (Lee-Sepsick et al.—inventors; Femasys, Inc.—Applicant) (4 Pages).
Request for Examination dated Oct. 11, 2014 for Brazilian Patent Application No. BR1120130114347 which claims priority to PCT/US2011/060013 filed Nov. 9, 2011 (Lee-Sepsick et al.—inventors; Femasys, Inc.—Applicant) (1 Page).
Office Action dated Jul. 31, 2014 for Chinese Patent Application No. 2011035992.2 which claims priority to PCT/US2011/060013 filed Nov. 9, 2011 (Lee-Sepsick et al.—inventors; Femasys, Inc.—Applicant) (11 Pages).
Office Action dated Jun. 3, 2015 for Chinese Patent Application No. 2011035992.2 which claims priority to PCT/US2011/060013 filed Nov. 9, 2011 (Lee-Sepsick et al.—inventors; Femasys, Inc.—Applicant) (8 Pages).
Office Action dated Feb. 16, 2016 for Chinese Patent Application No. 2011035992.2 which claims priority to PCT/US2011/060013 filed Nov. 9, 2011 (Lee-Sepsick et al.—inventors; Femasys, Inc.—Applicant) (11 Pages).
Request for Examination dated Nov. 5, 2014 for Indian Patent Application No. 5058DELNP/2013 which claims priority to PCT/US2011/060013 filed Nov. 9, 2011 (Lee-Sepsick et al.—inventors; Femasys, Inc.—Applicant) (1 Page).
Communication dated Nov. 21, 2017 for European Patent Application No. 11839530.0 which claims priority to PCT/US2011/060013 filed Nov. 9, 2011 (Lee-Sepsick et al.—inventors; Femasys, Inc.—Applicant) (6 Pages).
Supplemental Search and Opinion dated Oct. 17, 2014 for European Patent Application No. 11839530.0 which claims priority to PCT/US2011/060013 filed Nov. 9, 2011 (Lee-Sepsick et al.—inventors; Femasys, Inc.—Applicant) (11 Pages).
U.S. Appl. No. 11/065,886, filed Feb. 24, 2005, Kathy Lee-Sepsick.
U.S. Appl. No. 12/240,738, filed Sep. 29, 2008, Kathy Lee-Sepsick.
U.S. Appl. No. 12/240,791, filed Sep. 29, 2008, Kathy Lee-Sepsick.
U.S. Appl. No. 12/504,912, filed Jul. 17, 2009, Kathy Lee-Sepsick.
U.S. Appl. No. 13/285,744, filed Oct. 31, 2010, Kathy Lee-Sepsick.
U.S. Appl. No. 13/285,908, filed Oct. 31, 2010, Kathy Lee-Sepsick.
U.S. Appl. No. 13/286,127, filed Oct. 31, 2010, Kathy Lee-Sepsick.
U.S. Appl. No. 16/371,669, filed Apr. 1, 2019, Kathy Lee-Sepsick.
U.S. Appl. No. 16/186,553, filed Nov. 11, 2018, Kathy Lee-Sepsick.
United Nations Secretariat. (2003) Fertility, Contraception and population policies. United Nations Population Division, Department of Economic and Social Affairs. ESA/P/WP.182 (42 pages).

(56) References Cited

OTHER PUBLICATIONS

Abdala N, et al. (2001). Use of ethylene vinyl alcohol copolymer for tubal sterilization by selective catheterization in rabbits. J Vasc Interv Radiol. 12(8): 979-984.
Abma JC, et al. (1997) Fertility, family planning, and women's health: new data from the 1995 National Survey of Family Growth. Vital Health Stat 23. (19): 1-114.
Pollack A. (2003) ACOG practice bulletin. Clinical management guidelines for obstetrician-gynecologists. Obstet Gynecol. 102(3): 647-658.
American Foundation for Urologic Disease. (2005) Facts about vasectomy safety. Published by the National Institute of Child Health & Human Development. Retrieved at http://www.nichd.nih.gov/publications/pubs/vasect.htm on Jun. 29, 2005.
ApSimon HT, et al. (1984) Embolization of small vessels with a double-lumen microballoon catheter. Part I: Design and construction. Radiology. 151(1): 55-57.
Assaf A, et al. (1993) Histopathological effects of silicone rubber 'Ovabloc' on the human fallopian tube. Int J Gynaecol Obstet. 43(2): 181-189.
Basu S, et al. (1995) Comparative study of biological glues: cryoprecipitate glue, two-component fibrin sealant, and "French" glue. Ann Thorac Surg. 60(5): 1255-1262.
Berkey GS, et al. (1995) Sterilization with methyl cyanoacrylate-induced fallopian tube occlusion from a nonsurgical transvaginal approach in rabbits. J Vasc Interv Radiol. 6(5): 669-674.
Brundin J, et al. (1985) Long-term toxicity of a hydrogelic occlusive device in the isthmus of the human oviduct. A light microscopic study. Acta Pathol Microbiol Immunol Scand A. 93(3): 121-126.
Brundin J. (1991) Transcervical sterilization in the human female by hysteroscopic application of hydrogelic occlusive devices into the intramural parts of the fallopian tubes: 10 years experience of the P-block. Eur J Obstet Gynecol Reprod Biol. 39(1): 41-49.
Canavan TP. (1998) Appropriate use of the intrauterine device. Am Fam Physician. 58(9): 2077-2084, 2087-2088. Review.
Chen FQ. (1989) Study on the transperitoneal sterilization of the fallopian tube with silicon rubber plug and its reversibility. Shengzhi Yu Biyun. 9(3): 51-54. (Abstract Only).
Clenney TL, et al. (1999) Vasectomy techniques. Am Fam Physician. 60(1): 137-146, 151-152.
Cooper JM. (1992) Hysteroscopic sterilization. Clin Obstet Gynecol. 3 5(2): 282-298.
Dan SJ, et al. (1984) Fallopian tube occlusion with silicone: radiographic appearance. Radiology. 151(3): 603-605.
Davis RH, et al. (1979) Chronic occlusion of the monkey fallopian tube with silicone polymer. Obstet Gynecol. 53(4): 527-529.
Davis RH, et al. (1979) Chronic occlusion of the rabbit Fallopian tube with silicone polymer. Gynecol Obstet Invest. 10(6): 281-288.
Davis RH, et al. (1975) Fallopian tube occlusion in rabbits with silicone rubber. J Reprod Med. 14(2): 56-61.
El-Mowafi DM, et al. (2008) Fallopian Tube. Geneva Foundation for Medical Education and Research. (8 pages) Download available at: http://www.gfmer.ch/International_activities_En/E1_Mowafi/Fallopian_tube.htm.
Erb RA, et al. (1979) Hysteroscopic oviductal blocking with formed-in-place silicone rubber plugs. I. Method and apparatus. J Reprod Med. 23(2): 65-68.
Farcon E, et al. (1975) An absorbable intravasal stent and a silicone intravasal reversible plug. Report of experiments on animals. Invest Urol. 13(2): 108-112.
Fischer ME, et al. (1984) Silicone devices for tubal occlusion: radiographic description and evaluation. Radiology. 151(3): 601-602.
Grode GA, et al. (1971) Feasibility study on the use of a tissue adhesive for the nonsurgical blocking of fallopian tubes. Phase I: evaluation of a tissue adhesive. Fertil Steril. 22(9): 552-555.
Harrell WB, et al. (1969) Simulated tuboplasty using tissue adhesive on uterine horn in canines. J Ark Med Soc. 65(11): 433-435. (Abstract Only).

Hefnawi F, et al. (1967) Control of fertility by temporary occlusion of the oviduct. Am J Obstet Gynecol. 99(3): 421-427. (Abstract Only).
Hendrix NW, et al. (1999). Sterilization and its consequences. Obstet Gynecol Surv. 54(12): 766-777.
Holt VL, et al. (2003) Oral contraceptives, tubal sterilization, and functional ovarian cyst risk. Obstet Gynecol. 102(2): 252-258.
Huvar I, et al. (1994) Hysteroscopic sterilization using Ovabloc. Ceska Gynekol. 59(4): 193-195. (Abstract Only).
Jamieson DJ, et al. (2002) A comparison of women's regret after vasectomy versus tubal sterilization. Obstet Gynecol. 99(6): 1073-1079.
Keller MW, et al. (1986) Automated production and analysis of echo contrast agents. J Ultrasound Med. 5(9): 493-498.
Libenzon LL, et al. (1973) Contraception through the sealing off of Fallopian tubes (experimental studies). Eksp Khir Anesteziol. 18(5): 18-20.
Loffer FD, et al. (1986) Learning hysteroscopy sterilization and the Ovabloc System with Hyskon. Acta Eur Fertil. 17(6): 477-480. (Abstract Only).
Loffer FD. (1982) What's new in female sterilization? The silicone tubal plug is. Ariz Med. 39(7): 442-445. (Abstract Only).
Loffer FD. (1984) Hysteroscopic sterilization with the use of formed-in-place silicone plugs. Am J Obstet Gynecol. 149(3): 261-270. (Abstract Only).
Maubon AJ, et al. (1996) Tubal sterilization by means of selective catheterization: comparison of a hydrogel and a collagen glue. J Vasc Interv Radiol. 7(5): 733-736.
Neuwirth RS, et al. (1971) Chemical induction of tubal blockade in the monkey. Obstet Gynecol. 38(1): 51-54.
Neuwirth RS, et al. (1980) An outpatient approach to female sterilization with methylcyanoacrylate. Am J Obstet Gynecol. 136(7): 951-956.
Neuwirth RS, et al. (1983) Trials with the FEMCEPT method of female sterilization and experience with radiopaque methylcyanoacrylate. Am J Obstet Gynecol. 145(8): 948-954.
No authors listed. (1973) Animal studies show silicone plugs prevent conception. JAMA. 225(2): 105-106.
No authors listed. (1973) Implants seen as reversible contraceptives. Biomed News. 4: 12. (Abstract Only).
No authors listed. (Apr. 1994) Hysteroscopy. ACOG Technical Bulletin No. 191. Int J Gynaecol Obstet. 45(2): 175-180. (Abstract Only).
Omran KF, et al. (1970) Tubal occlusion: a comparative study. Int J Fertil. 15(4): 226-241.
Pelage JP, et al. (1998) Selective salpingography and fallopian tubal occlusion with n-butyl-2-cyanoacrylate: report of two cases. Radiology. 207(3): 809-812.
Rakshit B. (1970) Attempts at chemical blocking of the Fallopian tube for female sterilization. J Obstet Gynaecol India. 20: 618-624. (Abstract Only).
Reed TP et al. (1980) Tubal occlusion with silicone rubber: an update. J Reprod Med. 25(1): 25-28.
Reed TP, et al. (1983) Hysteroscopic tubal occlusion with silicone rubber. Obstet Gynecol. 61(3): 388-392.
Reed TP, et al. (Nov. 1978) Hysteroscopic Oviductal Blocking with Formed-In-Place Silicone Rubber Plugs Clinical Studies. Paper presented at the Clinical Symposium on Gynecologic Endoscopy. 7th Annual Meeting (Hollywood, FL) (pp. 1-4).
Richart RM. (1981) Female sterilization using chemical agents. Res Front Fertil Regul. 1(5): 1-12.
Richman TS, et al. (1984) Fallopian tubal patency assessed by ultrasound following fluid injection. Work in progress. Radiology. 152(2): 507-510.
Saito H, et al. (2007) pH-responsive swelling behavior of collagen gels prepared by novel crosslinkers based on naturally derived di- or tricarboxylic acids. Acta Biomater. 3(1): 89-94.
Snider S. (1990). The Pill: 30 years of Safety Concerns. Published by the U.S. Food and Drug Administration. (6 pages).
Steptoe PC. (1975) Advances in laparoscopic sterilisation techniques. S Afr Med J. 49(48): 2019-2021. (Abstract Only).

(56) References Cited

OTHER PUBLICATIONS

Stevenson TC, et al. (1972) The effect of methyl cyanoacrylate tissue adhesive on the human Fallopian tube and endometrium. J Obstet Gynaecol Br Commonw. 79(11): 1028-1039.
Su YK. (1991) Embolus formation using bismuth polyurethane for tubosterilization observation of 259 cases. Zhonghua Fu Chan Ke Za Zhi. 26(6): 352-354, 388. (Abstract Only).
Van der Leij G, et al. (1995) Impact of Ovabloc intratubal polymer on the morphology of the fallopian tube. Int J Gynecol Pathol. 14(2): 167-173.
Van der Leij G, et al. (1997) Radiographic aspects of office hysteroscopic tubal occlusion with siloxane intratubal devices (the Ovabloc method). Int J Gynaecol Obstet. 59(2): 123-131.
Viddya Medical News Service. (2000) Bibliography Excerpts: Side effects of tubal ligation sterilizations. 1: 249. (5 pages).
Volpi E, et al. (1996). Transvaginal sonographic tubal patency testing using air and saline solution as contrast media in a routine infertility clinic setting. Ultrasound Obstet Gynecol. 7(1): 43-48.
Wilson EW. (1995) The evolution of methods for female sterilization. Int J Gynaecol Obstet. 51 Suppl 1: S3-13.
Issue Notification dated Oct. 12, 11 for U.S. Appl. No. 11/065,886, filed Feb. 24, 2005 (Lee-Sepsick et al.—inventors) (1 page).
Notice of Allowance dated Jul. 15, 2011 for U.S. Appl. No. 11/065,886, filed Feb. 24, 2005 (Lee-Sepsick et al.—inventors) (11 pages).
Response to Non-Final Office Action filed Apr. 19, 2011 for U.S. Appl. No. 11/065,886, filed Feb. 24, 2005 (Lee-Sepsick et al.—inventors) (17 pages).
Draft Claim Language faxed Mar. 15, 2011 for U.S. Appl. No. 11/065,886, filed Feb. 24, 2005 (Lee-Sepsick et al.—inventors) (4 pages).
Non-Final Office Action issued Jan. 19, 2011 for U.S. Appl. No. 11/065,886, filed Feb. 24, 2005 (Lee-Sepsick et al.—inventors) (25 pages).
Response to Final Office Action filed Sep. 23, 2010 for U.S. Appl. No. 11/065,886, filed Feb. 24, 2005 (Lee-Sepsick et al.—inventors) (30 pages).
Advisory Action dated Jul. 15, 2010 for U.S. Appl. No. 11/065,886, filed Feb. 24, 2005 (Lee-Sepsick et al.—inventors) (8 pages).
Response to Final Office Action filed Jun. 24, 2010 for U.S. Appl. No. 11/065,886, filed Feb. 24, 2005 (Lee-Sepsick et al.—inventors) (26 pages).
Notice of Appeal filed Jun. 24, 2010 for U.S. Appl. No. 11/065,886, filed Feb. 24, 2005 (Lee-Sepsick et al.—inventors) (1 page).
Examiner Interview Summary dated May 25, 2010 for U.S. Appl. No. 11/065,886, filed Feb. 24, 2005 (Lee-Sepsick et al.—inventors) (4 pages).
Final Office Action dated Dec. 24, 2009 for U.S. Appl. No. 11/065,886, filed Feb. 24, 2005 (Lee-Sepsick et al.—inventors) (29 pages).
Response to Non-Final Office Action filed Sep. 24, 2009 U.S. Appl. No. 11/065,886, filed Feb. 24, 2005 (Lee-Sepsick et al.—inventors) (22 pages).
Examiner Interview Summary dated Jun. 30, 2009 for U.S. Appl. No. 11/065,886, filed Feb. 24, 2005 (Lee-Sepsick et al.—inventors) (2 pages).
Non-Final Office Action dated Jun. 24, 2009 for U.S. Appl. No. 11/065,886, filed Feb. 24, 2005 (Lee-Sepsick et al.—inventors) (26 pages).
Response to Restriction Requirement filed Apr. 21, 2009 for U.S. Appl. No. 11/065,886, filed Feb. 24, 2005 (Lee-Sepsick et al.—inventors) (10 pages).
Restriction Requirement dated Mar. 23, 2009 for U.S. Appl. No. 11/065,886, filed Feb. 24, 2005 (Lee-Sepsick et al.—inventors) (5 pages).
Issue Notification dated Oct. 12, 2011 for U.S. Appl. No. 12/240,738, filed Sep. 29, 2008 (Lee-Sepsick et al.—inventors) (1 page).
Notice of Allowance and Fee(s) Due dated Jul. 25, 2011 for U.S. Appl. No. 12/240,738, filed Sep. 29, 2008 (Lee-Sepsick et al.—inventors) (9 pages).
Terminal Disclaimer (with Review) filed Jul. 10, 2011 for U.S. Appl. No. 12/240,738, filed Sep. 29, 2008 (Lee-Sepsick et al.—inventors) (3 pages).
Terminal Disclaimer (with Review) filed Jun. 24, 2011 for U.S. Appl. No. 12/240,738, filed Sep. 29, 2008 (Lee-Sepsick et al.—inventors) (3 pages).
Response to Non-Final Office Action filed Apr. 21, 2011 for U.S. Appl. No. 12/240,738, filed Sep. 29, 2008 (Lee-Sepsick et al.—inventors) (15 pages).
Non-Final Office Action dated Dec. 21, 2010 for U.S. Appl. No. 12/240,738, filed Sep. 29, 2008 (Lee-Sepsick et al.—inventors) (22 pages).
Response to Restriction Requirement filed Oct. 11, 2010 for U.S. Appl. No. 12/240,738, filed Sep. 29, 2008 (Lee-Sepsick et al.—inventors) (7 pages).
Restriction Requirement dated Jun. 9, 2010 for U.S. Appl. No. 12/240,738, filed Sep. 29, 2008 (Lee-Sepsick et al.—inventors) (6 pages).
Issue Notification dated Oct. 19, 2010 for U.S. Appl. No. 12/240,791, filed Sep. 29, 2008 (Lee-Sepsick et al.—inventors) (1 page).
Notice of Allowance dated Jul. 21, 2011 for U.S. Appl. No. 12/240,791, filed Sep. 29, 2008 (Lee-Sepsick et al.—inventors) (12 pages).
Terminal Disclaimer (with Review) filed Jun. 24, 2011 for U.S. Appl. No. 12/240,791, filed Sep. 29, 2008 (Lee-Sepsick et al.—inventors) (3 pages).
Response to Non-Final Office Action filed Apr. 21, 2011 for U.S. Appl. No. 12/240,791, filed Sep. 29, 2008 (Lee-Sepsick et al.—inventors) (10 pages).
Non-Final Office Action dated Dec. 21, 2010 for U.S. Appl. No. 12/240,791, filed Sep. 29, 2008 (Lee-Sepsick et al.—inventors) (15 pages).
Response to Restriction Requirement filed Oct. 11, 2010 for U.S. Appl. No. 12/240,791, filed Sep. 29, 2008 (Lee-Sepsick et al.—inventors) (6 pages).
Restriction Requirement dated Jun. 9, 2010 for U.S. Appl. No. 12/240,791, filed Sep. 29, 2008 (Lee-Sepsick et al.—inventors) (6 pages).
Notice of Allowance dated Jul. 19, 2012 for U.S. Appl. No. 12/504,912, filed Jul. 17, 2009 (Lee-Sepsick et al.—inventors) (7 pages).
Notice of Allowance dated Mar. 14, 2012 for U.S. Appl. No. 12/504,912, filed Jul. 17, 2009 (Lee-Sepsick et al.—inventors) (15 pages).
Terminal Disclaimer Review issued Feb. 10, 2012 for U.S. Appl. No. 12/504,912, filed Jul. 17, 2009 (Lee-Sepsick et al.—inventors) (15 pages).
Response to Final Office Action with Terminal Disclaimer filed Feb. 9, 2012 for U.S. Appl. No. 12/504,912, filed Jul. 17, 2009 (Lee-Sepsick et al.—inventors) (6 pages).
Final Office Action dated Jan. 6, 2012 for U.S. Appl. No. 12/504,912, filed Jul. 17, 2009 (Lee-Sepsick et al.—inventors) (9 pages).
Response to Non-Final Office Action filed Nov. 4, 2011 for U.S. Appl. No. 12/504,912, filed Jul. 17, 2009 (Lee-Sepsick et al.—inventors) (10 pages).
Non-Final Office Action dated Aug. 4, 2011 for U.S. Appl. No. 12/504,912, filed Jul. 17, 2009 (Lee-Sepsick et al.—inventors) (15 pages).
Notice of Allowance dated Jul. 25, 2012 for U.S. Appl. No. 13/285,744, filed Oct. 31, 2011 (Lee-Sepsick et al.—inventors) (7 pages).
Response to Non-Final Office Action filed Jul. 2, 2012 for U.S. Appl. No. 13/285,744, filed Oct. 31, 2011 (Lee-Sepsick et al.—inventors) (7 pages).
Final Office Action dated Feb. 17, 2012 for U.S. Appl. No. 13/285,744, filed Oct. 31, 2011 (Lee-Sepsick et al.—inventors) (8 pages).
Terminal Disclaimer Review issued Mar. 21, 2012 for U.S. Appl. No. 13/285,744, filed Oct. 31, 2011 (Lee-Sepsick et al.—inventors) (1 page).
Response to Non-Final Office Action with Terminal Disclaimers filed Mar. 16, 2012 for U.S. Appl. No. 13/285,744, filed Oct. 31, 2011 (Lee-Sepsick et al.—inventors) (10 pages).

(56) References Cited

OTHER PUBLICATIONS

Non-Final Office Action dated Feb. 17, 2012 for U.S. Appl. No. 13/285,744, filed Oct. 31, 2011 (Lee-Sepsick et al.—inventors) (11 pages).
Preliminary Amendment filed Oct. 31, 2011 for U.S. Appl. No. 13/285,744, filed Oct. 31, 2011 (Lee-Sepsick et al.—inventors) (7 pages).
Terminal Disclaimer Review issued Jul. 30, 2012 for U.S. Appl. No. 13/285,744, filed Oct. 31, 2011 (Lee-Sepsick et al.—inventors) (1 pages).
Response to Non-Final Office Action with Terminal Dissclaimers filed Jul. 26, 2012 for U.S. Appl. No. 13/285,744, filed Oct. 31, 2011 (Lee-Sepsick et al.—inventors) (11 pages).
Non-Final Office Action dated Apr. 26, 2012 for U.S. Appl. No. 13/285,744, filed Oct. 31, 2011 (Lee-Sepsick et al.—inventors) (9 pages).
Terminal Disclaimer Review issued Jul. 5, 2012 for U.S. Appl. No. 13/286,127, filed Oct. 31, 2011 (Lee-Sepsick et al.—inventors) (1 page).
Response to Non-Final Office Action with Terminal Dissclaimers filed Jul. 2, 2012 for U.S. Appl. No. 13/286,127, filed Oct. 31, 2011 (Lee-Sepsick et al.—inventors) (9 pages).
Non-Final Office Action dated Mar. 30, 2012 for U.S. Appl. No. 13/286,127, filed Oct. 31, 2011 (Lee-Sepsick et al.—inventors) (8 pages).
Preliminary Amendment filed Oct. 31, 2011 for U.S. Appl. No. 13/286,127, filed Oct. 31, 2011 (Lee-Sepsick et al.—inventors) (7 pages).
Response to Third Office Action filed Sep. 6, 2010 for Chinese Application No. CN 200580006068.X, which claims priority to PCT/US2005/006334 filed on Feb. 25, 2005 (Lee-Sepsick et al. listed as inventors and Femasys Inc. listed as Applicant).
Third Office Action dated Jun. 24, 2010 for Chinese Application No. CN 200580006068.X, which claims priority to PCT/US2005/006334 filed on Feb. 25, 2005 (Lee-Sepsick et al. listed as inventors and Femasys Inc. listed as Applicant).
Response to Second Office Action filed Apr. 24, 2009 for Chinese Application No. CN 200580006068.X, which claims priority to PCT/US2005/006334 filed on Feb. 25, 2005 (Lee-Sepsick et al. listed as inventors and Femasys Inc. listed as Applicant).
Second Office Action dated Dec. 12, 2008 for Chinese Application No. CN 200580006068.X, which claims priority to PCT/US2005/006334 filed on Feb. 25, 2005 (Lee-Sepsick et al. listed as inventors and Femasys Inc. listed as Applicant).
Response to First Office Action filed Jun. 16, 2008 for Chinese Application No. CN 200580006068.X, which claims priority to PCT/US2005/006334 filed on Feb. 25, 2005 (Lee-Sepsick et al. listed as inventors and Femasys Inc. listed as Applicant).
First Office Action dated Nov. 30, 2007 for Chinese Application No. CN 200580006068.X, which claims priority to PCT/US2005/006334 filed on Feb. 25, 2005 (Lee-Sepsick et al. listed as inventors and Femasys Inc. listed as Applicant).
Examination Report dated Nov. 8, 2011 for Canadian Application No. CA 2556747, which claims priority to PCT/US2005/006334 filed on Feb. 25, 2005 (Lee-Sepsick et al.—inventors; Femasys Inc.—Applicant) (2 pages).
Amended Claims filed Oct. 19, 2011 for Canadian Application No. CA 2556747, which claims priority to PCT/US2005/006334 filed on Feb. 25, 2005 (Lee-Sepsick et al.—inventors; Femasys Inc.—Applicant) (11 pages).
Examination Report dated Apr. 19, 2011 for Canadian Application No. CA 2556747, which claims priority to PCT/US2005/006334 filed on Feb. 25, 2005 (Lee-Sepsick et al.—inventors; Femasys Inc.—Applicant) (3 pages).
Voluntary Amendments filed Mar. 1, 2010 for Canadian Application No. CA 2556747, which claims priority to PCT/US2005/006334 filed on Feb. 25, 2005 (Lee-Sepsick et al. listed as inventors and Femasys Inc. listed as Applicant) (16 pages).
Response to Article 94(3) Communication filed Feb. 6, 2012 for European Patent Application No. 05723981.3, which claims priority to PCT/US2005/006334 filed on Feb. 25, 2005 (Lee-Sepsick et al.—inventors; Femasys Inc.—Applicant) (20 pages).
Communication pursuant to Article 94(3) dated Jul. 8, 2011 for European Patent Application No. 05723981.3, which claims priority to PCT/US2005/006334 filed on Feb. 25, 2005 (Lee-Sepsick et al.—inventors; Femasys Inc.—Applicant) (5 pages).
Response filed Sep. 2, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (3 pages).
Response filed Jul. 12, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (11 pages).
Response filed Apr. 13, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (1 page).
Response filed Apr. 5, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (9 pages).
Office Action dated Apr. 21, 2010 for Indian Application No. 2536/KOLNP/2006, which claims priority to PCT/US2005/006334 filed on Feb. 25, 2005 (Lee-Sepsick et al.—inventors; Femasys Inc.—Applicant) (2 pages).
Certificate of Patent issued May 27, 2011 for Japanese Application No. JP2007-500782, which claims priority to PCT/US2005/006334 filed on Feb. 25, 2005 (Lee-Sepsick et al.—inventors; Femasys Inc.—Applicant) (2 pages).
Decision to Grant dated Apr. 19, 2011 for Japanese Application No. JP2007-500782, which claims priority to PCT/US2005/006334 filed on Feb. 25, 2005 (Lee-Sepsick et al.—inventors; Femasys Inc.—Applicant) (1 page).
Response to Office Action filed Nov. 4, 2010 for Japanese Application No. JP2007-500782, which claims priority to PCT/US2005/006334 filed on Feb. 25, 2005 (Lee-Sepsick et al. listed as inventors and Femasys Inc. listed as Applicant).
Office Action dated May 11, 2010 for Japanese Application No. JP2007-500782, which claims priority to PCT/US2005/006334 filed on Feb. 25, 2005 (Lee-Sepsick et al. listed as inventors and Femasys Inc. listed as Applicant).
International Search Report dated Sep. 22, 2005 for PCT Application No. PCT/US2005/006334 filed on Feb. 25, 2005, which published as WO/2005/082299 on Sep. 9, 2005 (Lee-Sepsick et al. listed as inventors and Femasys Inc. listed as Applicant) (8 pages).
Written Opinion dated Sep. 22, 2005 for PCT Application No. PCT/US2005/006334 filed on Feb. 25, 2005, which published as WO/2005/082299 on Sep. 9, 2005 (Lee-Sepsick et al. listed as inventors and Femasys Inc. listed as Applicant) (4 pages).
International Preliminary Report on Patentability dated Aug. 30, 2006 for PCT Application No. PCT/US2005/006334 filed on Feb. 25, 2005, which published as WO/2005/082299 on Sep. 9, 2005 (Lee-Sepsick et al. listed as inventors and Femasys Inc. listed as Applicant) (5 pages).
Response to Communication pursuant to Rules 161(1) and 162 EPC filed Feb. 13, 2012 for EP 09793278.4, which claims priority to PCT/US2009/059370 filed on Oct. 2, 2009 and published as WO 2010/040046 on Apr. 8, 2010 (Lee-Sepsick et al.—inventors; Femasys Inc.—applicant) (15 pages).
Communication pursuant to Rules 161(1) and 162 EPC dated Aug. 4, 2011 for EP 09793278.4, which claims priority to PCT/US2009/059370 filed on Oct. 2, 2009 and published as WO 2010/040046 on Apr. 8, 2010 (Lee-Sepsick et al.—inventors; Femasys Inc.—applicant) (2 pages).
International Preliminary Report on Patentability dated Apr. 5, 2011 for PCT/US2009/059370 filed on Oct. 2, 2019, which published as WO 2010/040046 on Apr. 8, 2010 (Lee-Sepsick et al. listed as inventors and Femasys Inc. listed as Applicant) (7 pages).
International Search Report dated Jan. 22, 2010 for PCT/US2009/059370 filed on Oct. 2, 2019, which published as WO 2010/040046 on Apr. 8, 2010 (Lee-Sepsick et al. listed as inventors and Femasys Inc. listed as Applicant) (6 pages).

(56) References Cited

OTHER PUBLICATIONS

Written Opinion dated Jan. 22, 2010 for PCT/US2009/059370 filed on Oct. 2, 2019, which published as WO 2010/040046 on Apr. 8, 2010 (Lee-Sepsick et al. listed as inventors and Femasys Inc. listed as Applicant) (6 pages).
International Search Report and Written Opinion dated Mar. 23, 2012 for PCT/US2011/060013 filed on Nov. 9, 2011, which published as WO 2012/064866 on May 15, 2012 (Lee-Sepsick et al. listed as inventors and Femasys Inc. listed as Applicant) (12 pages).
Issue Notification dated Nov. 7, 2011 for U.S. Appl. No. 12/504,912, filed Nov. 27, 2012, (Lee-Sepsick et al.—inventors) (1 page).
Issue Notification dated Nov. 7, 2011 for U.S. Appl. No. 13/285,744, filed Nov. 27, 2012 (Lee-Sepsick et al.—inventors) (1 page).
Issue Notification dated Dec. 5, 2012 for U.S. Appl. No. 13/285,908, filed Dec. 25, 2012 (Lee-Sepsick et al.—inventors) (1 page).
Notice of Allowance dated Sep. 4, 2012 for U.S. Appl. No. 13/285,908, filed Dec. 25, 2012 (Lee-Sepsick et al.—inventors) (9 pages).
Terminal Disclaimer Review issued Jul. 30, 2012 for U.S. Appl. No. 13/285,908, filed Dec. 25, 2012 (Lee-Sepsick et al.—inventors) (1 page).
Response to Non-Final Office Action dated Jul. 26, 2012 U.S. Appl. No. 13/285,908, filed Dec. 25, 2012 (Lee-Sepsick et al.—inventors) (11 pages).
Non-Final Office Action dated Apr. 26, 2012 for U.S. Appl. No. 13/285,908, filed Dec. 25, 2012 (Lee-Sepsick et al.—inventors) (8 pages).
Preliminary Amendment filed Oct. 31, 2011 for U.S. Appl. No. 13/285,908, filed Dec. 25, 2012 (Lee-Sepsick et al.—inventors) (7 pages).
Issue Notification dated Nov. 14, 2012 for U.S. Appl. No. 13/286,127, filed Dec. 4, 2012 (Lee-Sepsick et al.—inventors) (1 page).
Response to 312 Notice of Allowance dated Sep. 17, 2012 for U.S. Appl. No. 13/286,127, filed Dec. 4, 2012 (Lee-Sepsick et al.—inventors) (2 pages).
Amendment after Notice of Allowance dated Aug. 29, 2012 for U.S. Appl. No. 13/286,127, filed Dec. 4, 2012 (Lee-Sepsick et al.—inventors) (2 pages).
Amendment after Notice of Allowance dated Aug. 28, 2012 for U.S. Appl. No. 13/286,127, filed Dec. 4, 2012 (Lee-Sepsick et al.—inventors) (3 pages).
Notice of Allowance dated Aug. 8, 2012 for U.S. Appl. No. 13/286,127, filed Dec. 4, 2012 (Lee-Sepsick et al.—inventors) (8 pages).
Response after Non-Final Action dated Jul. 2, 2012 for U.S. Appl. No. 13/286,127, filed Dec. 4, 2012 (Lee-Sepsick et al.—inventors) (10 pages).
Terminal Disclaimer Review issued Jul. 5, 2012 for U.S. Appl. No. 13/286,127, filed Dec. 4, 2012 (Lee-Sepsick et al.—inventors) (1 page).
Non-Final Office Action dated Mar. 30, 2012 for U.S. Appl. No. 13/286,127, filed Dec. 4, 2012 (Lee-Sepsick et al.—inventors) (38 pages).
Preliminary Amendment dated Oct. 31, 2011 for U.S. Appl. No. 13/286,127, filed Dec. 4, 2012 (Lee-Sepsick et al.—inventors) (5 pages).
Issue Notification dated Mar. 26, 2014 for U.S. Appl. No. 13/684,524, filed Nov. 24, 2012 (Lee-Sepsick et al.—inventors) (1 page).
Notice of Allowance dated Nov. 15, 2013 for U.S. Appl. No. 13/684,524, filed Nov. 24, 2012 (Lee-Sepsick et al.—inventors) (9 pages).
Terminal Disclaimer Review issued Oct. 21, 2013 for U.S. Appl. No. 13/684,524, filed Nov. 24, 2012 (Lee-Sepsick et al.—inventors) (4 pages).
Response to Non-Final Office Action dated Oct. 21, 2013 for U.S. Appl. No. 13/684,524, filed Nov. 24, 2012 (Lee-Sepsick et al.—inventors) (9 pages).
Preliminary Amendment dated May 14, 2013 for U.S. Appl. No. 13/684,524, filed Nov. 24, 2012 (Lee-Sepsick et al.—inventors) (6 pages).
Issue Notification dated Apr. 29, 2015 for U.S. Appl. No. 13/684,529, filed Nov. 24, 2012 (Lee-Sepsick et al.—inventors) (1 page).
Notice of Allowance dated Apr. 1, 2015 for U.S. Appl. No. 13/684,529, filed Nov. 24, 2012 (Lee-Sepsick et al.—inventors) (8 pages).
Request for Continued Examination dated Mar. 13, 205 for U.S. Appl. No. 13/684,529, filed Nov. 24, 2012 (Lee-Sepsick et al.—inventors) (1 page).
Notice of Allowance dated Jan. 16, 2015 for U.S. Appl. No. 13/684,529, filed Nov. 24, 2012 (Lee-Sepsick et al.—inventors) (8 pages).
Response after Final Action dated Dec. 11, 2014 for U.S. Appl. No. 13/684,529, filed Nov. 24, 2012 (Lee-Sepsick et al.—inventors) (9 pages).
Final Rejection dated Oct. 23, 2014 for U.S. Appl. No. 13/684,529, filed Nov. 24, 2012 (Lee-Sepsick et al.—inventors) (10 pages).
Response after Non-Final Office Action dated Jul. 3, 2014 for U.S. Appl. No. 13/684,529, filed Nov. 24, 2012 (Lee-Sepsick et al.—inventors) (16 pages).
Non-Final Office Action dated Jan. 3, 2014 for U.S. Appl. No. 13/684,529, filed Nov. 24, 2012 (Lee-Sepsick et al.—inventors) (16 pages).
Preliminary Amendment dated May 16, 2013 for U.S. Appl. No. 13/684,529, filed Nov. 24, 2012 (Lee-Sepsick et al.—inventors) (7 pages).
Issue Notification dated Apr. 30, 2014 for U.S. Appl. No. 13/268,4546, filed Nov. 25, 2012 (Lee-Sepsick et al.—inventors) (1 page).
Corrected Notice of Allowability dated May 15, 2014 for U.S. Appl. No. 13/2684546, filed Nov. 25, 2012 (Lee-Sepsick et al.—inventors) (2 pages).
Notice of Allowance dated Dec. 23, 2013 for U.S. Appl. No. 13/2684546, filed Nov. 25, 2012 (Lee-Sepsick et al.—inventors) (9 pages).
Terminal Disclaimer Approval issued Dec. 6, 2013 for U.S. Appl. No. 13/2684546, filed Nov. 25, 2012 (Lee-Sepsick et al.—inventors) (3 pages).
Response to Non-Final Office Action dated Dec. 6, 2013 for U.S. Appl. No. 13/2684546, filed Nov. 25, 2012 (Lee-Sepsick et al.—inventors) (15 pages).
Non-Final Office Action dated Sep. 6, 2013 for U.S. Appl. No. 13/2684546, filed Nov. 25, 2012 (Lee-Sepsick et al.—inventors) (10 pages).
Preliminary Amendments dated Nov. 25, 2012 for U.S. Appl. No. 13/2684546, filed Nov. 25, 2012 (Lee-Sepsick et al.—inventors) (7 pages).
Issue Notification dated Dec. 9, 2015 for U.S. Appl. No. 13/684,549, filed Nov. 25, 2012 (Lee-Sepsick et al.—inventors) (1 page).
Notice of Allowance dated Aug. 28, 2015 for U.S. Appl. No. 13/684,549, filed Nov. 25, 2012 (Lee-Sepsick et al.—inventors) (10 pages).
Response to Non-Final Office Action dated Jul. 23, 2015 for U.S. Appl. No. 13/684,549, filed Nov. 25, 2012 (Lee-Sepsick et al.—inventors) (8 pages).
Non-Final Office Action dated Apr. 23, 2015 for U.S. Appl. No. 13/684,549, filed Nov. 25, 2012 (Lee-Sepsick et al.—inventors) (7 pages).
Response to Restriction Requirement dated Mar. 23, 2015 for U.S. Appl. No. 13/684,549, filed Nov. 25, 2012 (Lee-Sepsick et al.—inventors) (10 pages).
Restriction Requirement dated Jan. 23, 2015 for U.S. Appl. No. 13/684,549, filed Nov. 25, 2012 (Lee-Sepsick et al.—inventors) (10 pages).
Issue Notification dated Jul. 13, 2016 for U.S. Appl. No. 14/231,261, filed Mar. 31, 2014 (Lee-Sepsick et al.—inventors) (1 page).
Notice of Allowance dated Apr. 7, 2016 for U.S. Appl. No. 14/231,261, filed Mar. 31, 2014 (Lee-Sepsick et al.—inventors) (8 pages).
Response after Non-Final Response dated Feb. 23, 2016 for U.S. Appl. No. 14/231,261, filed Mar. 31, 2014 (Lee-Sepsick et al.—inventors) (11 pages).
Non-Final Office Action dated Oct. 23, 2015 for U.S. Appl. No. 14/231,261, filed Mar. 31, 2014 (Lee-Sepsick et al.—inventors) (8 pages).

(56) References Cited

OTHER PUBLICATIONS

Preliminary Amendment dated Mar. 26, 2015 for U.S. Appl. No. 14/231,261, filed Mar. 31, 2014 (Lee-Sepsick et al.—inventors) (4 pages).
Issue Notification dated Mar. 23, 2016 for U.S. Appl. No. 14/705,390, filed May 6, 2015 (Lee-Sepsick et al.—inventors) (1 page).
International Search Report, dated Jan. 22, 2010, for PCT Application No. PCT/US2009/059370, filed Oct. 2, 2009, (Femasys, Inc.—Applicant) (6 pages).
Written Opinion, dated Jan. 22, 2010, for PCT Application No. PCT/US2009/059370, filed Oct. 2, 2009, (Femasys, Inc.—Applicant) (6 pages).
IPRP, issued Apr. 5, 2011, for PCT Application No. PCT/US2009/059370, filed Oct. 2, 2009, (Femasys, Inc.—Applicant) (7 pages).
International Search Report, dated Mar. 23, 2012, for PCT Application No. PCT/US2011/060013, filed Nov. 9, 2011, (Femasys, Inc.—Applicant) (2 pages).
Written Opinion, dated Mar. 23, 2012, for PCT Application No. PCT/US2011/060013, filed Nov. 9, 2011, (Femasys, Inc.—Applicant) (6 pages).
IPRP, issued May 14, 2014, for PCT Application No. PCT/US2011/060013, filed Nov. 9, 2011, (Femasys, Inc.—Applicant) (7 pages).
Request for Examination, dated Oct. 26, 2016, for Korean Patent Application No. 2013-7014341, which claims priority to PCT/US2011/060013 filed Nov. 9, 2011 (Lee-Sepsick et al.—inventors; Femasys, Inc.—Applicant) (2 Pages).
First Office Action, dated Jan. 22, 2018, for Korean Patent Application No. 2013-7014341, which claims priority to PCT/US2011/060013 filed Nov. 9, 2011 (Lee-Sepsick et al.—inventors; Femasys, Inc.—Applicant) (7 Pages).
Request Examination dated Nov. 7, 2014 for Japanese Patent Application No. 2011-245163 which claims priority to PCT/US2011/060013 filed Nov. 9, 2011 (Lee-Sepsick et al.—inventors; Femasys, Inc.—Applicant) (1 Page).
Office Action dated Oct. 13, 2015 for Japanese Patent Application No. 2011-245163 which claims priority to PCT/US2011/060013 filed Nov. 9, 2011 (Lee-Sepsick et al.—inventors; Femasys, Inc.—Applicant) (2 Pages).
Office Action dated Feb. 2, 2016 for Japanese Patent Application No. 2011-245163 which claims priority to PCT/US2011/060013 filed Nov. 9, 2011 (Lee-Sepsick et al.—inventors; Femasys, Inc.—Applicant) (2 Pages).
Response to Non-Final Office Action dated May 24, 2018 for U.S. Appl. No. 15/793,306, filed Oct. 25, 2017 (Lee-Sepsick et al.—inventors) (10 pages).
Notice of Allowance, dated Jun. 29, 2018, for U.S. Appl. No. 15/793,306, filed Oct. 25, 2017 (Lee-Sepsick et al.—inventors) (8 pages).
Notice of Allowance, dated Sep. 19, 2018, for U.S. Appl. No. 15/793,306, filed Oct. 25, 2017 (Lee-Sepsick et al.—inventors) (4 pages).
Issue Notification, dated Oct. 10, 2018, for U.S. Appl. No. 15/793,306, filed Oct. 25, 2017 (Lee-Sepsick et al.—inventors) (1 page).
Issue Notification, dated May 1, 2019, for U.S. Appl. No. 16/144,033, filed Sep. 27, 2018 (Lee-Sepsick et al.—inventors) (1 page).
Notice of Allowance, dated Feb. 1, 2019, for U.S. Appl. No. 16/144,033, filed Sep. 27, 2018 (Lee-Sepsick et al.—inventors) (8 pages).
Response to NonFinal Office Action, dated Nov. 30, 2019, for U.S. Appl. No. 16/144,033, filed Sep. 27, 2018 (Lee-Sepsick et al.—inventors) (7 pages).
NonFinal Office Action, dated Nov. 27, 2019, for U.S. Appl. No. 16/144,033, filed Sep. 27, 2018 (Lee-Sepsick et al.—inventors) (24 pages).
Preliminary Amendment, dated Nov. 6, 2018, for U.S. Appl. No. 16/144,033, filed Sep. 27, 2018 (Lee-Sepsick et al.—inventors) (5 pages).
Response to NonFinal Office Action, dated Nov. 25, 2019, for U.S. Appl. No. 16/1371,669, filed Apr. 1, 2019 (Lee-Sepsick et al.—inventors) (10 pages).
NonFinal Office Action, dated Jul. 25, 2019, for U.S. Appl. No. 16/1371,669, filed Apr. 1, 2019 (Lee-Sepsick et al.—inventors) (23 pages).
Preliminary Amendment, dated Apr. 1, 2019, for U.S. Appl. No. 16/1371,669, filed Apr. 1, 2019 (Lee-Sepsick et al.—inventors) (5 pages).
Office Action, dated Oct. 24, 2019, for BR Application No. 1120130114347, filed Nov. 9, 2011, (Lee-Sepsick et al.—inventors) (4 pages).
Office Action, dated Jun. 25, 2019, for IN Application No. 5058DELNP/2013, filed Nov. 9, 2019,(Lee-Sepsick et al.—inventors) (6 pages).
Office Action, dated Jun. 20, 2019, for CA Application No. 2817296, filed Nov. 9, 2019,(Lee-Sepsick et al.—inventors) (3 pages).
Issue Notification, dated Mar. 27, 2019, for U.S. Appl. No. 16/043,996, filed Jul. 24, 2018 (Lee-Sepsick et al.—inventors) (1 page).
Notice of Allowance, dated Dec. 31, 2018, for U.S. Appl. No. 16/043,996, filed Jul. 24, 2018 (Lee-Sepsick et al.—inventors) (6 pages).
Response to NonFinal Office Action, dated Dec. 6, 2018, for U.S. Appl. No. 16/043,996, filed Jul. 24, 2018 (Lee-Sepsick et al.—inventors) (7 pages).
NonFinal Office Action, dated Sep. 6, 2018, for U.S. Appl. No. 16/043,996, filed Jul. 24, 2018 (Lee-Sepsick et al.—inventors) (11 pages).
Preliminary Amendment, dated Jul. 24, 2018, for U.S. Appl. No. 16/043,996, filed Jul. 24, 2018 (Lee-Sepsick et al.—inventors) (5 pages).
Response to NonFinal Office Action, dated Sep. 23, 2018, for U.S. Appl. No. 15/404,887, filed Jan. 12, 2017 (Lee-Sepsick et al.—inventors) (4 pages).
Notice of Allowance, dated Sep. 28, 2018, for U.S. Appl. No. 15/404,887, filed Jan. 12, 2017 (Lee-Sepsick et al.—inventors) (11 pages).
Issue Notification, dated Dec. 19, 2018, for U.S. Appl. No. 15/404,887, filed Jan. 12, 2017 (Lee-Sepsick et al.—inventors) (1 page).

METHODS AND DEVICES FOR SONOGRAPHIC IMAGING

CROSS-REFERENCE TO RELATED APPLICATIONS

This application is a continuation of U.S. patent application Ser. No. 16/043,996, filed Jul. 24, 2018, now U.S. patent Ser. No. 10/258,375, which is a continuation of U.S. patent application Ser. No. 12/245,265, filed Oct. 3, 2008, now U.S. patent Ser. No. 10/070,888, each of which is herein incorporated by reference in its entirety.

TECHNICAL FIELD

The present invention relates to methods and devices for sonographic imaging of organs, ducts and cavities. In particular, methods and devices of the present invention use detectable acoustic variations of alternating patterns of a gas phase and a liquid phase traversing a passage.

BACKGROUND OF THE INVENTION

Non-surgical diagnostic procedures for examining body ducts and cavities, in particular the uterus and Fallopian tubes, are well known. One procedure, known as hysterosalpingography, employs contrast agents and diagnostic fluoroscopic imaging techniques for viewing the uterus and Fallopian tubes. A safer, cheaper and easier method is hysterosonosalpingography, where ultrasound is utilized as the imaging modality. Ultrasound imaging also allows for evaluation of the uterine cavity using saline as a method of choice without assessment of Fallopian tube patency. Tubal patency and tubal occlusion can be assessed only under ideal sonographic conditions, limiting its usefulness clinically. Currently, no contrast agent indicated for contrast enhancement during ultrasound evaluation of the uterine cavity and Fallopian tubes is available in the U.S. Other ultrasound contrast agents are available for widespread use but are limited to use in cardiac and vascular applications. Most of the currently available vascular contrast agents are stabilized against dissolution and coalescence by the presence of additional materials, such as an elastic solid shell that enhances stability, or a surfactant or a combination of two or more surfactants. Contrast agents can improve the image quality of sonography either by decreasing the reflectivity of the undesired interfaces or by increasing the backscattered echoes from the desired regions. In the former approach, the contrast agents are taken orally, and for the latter effect, the agent is introduced vascularly. To pass through the lung capillaries and enter into the systemic circulation, microbubbles within a vascular contrast agent should be less than 10 microns in diameter (2 to 5 microns on average for most of the newer agents). Stability and persistence become major issues for such small microbubbles and air bubbles in this size range persist in solution for only a short time. Hence the gas bubbles have to be stabilized for the agent to persist long enough and survive pressure changes in the heart for systemic vascular use. Therefore, availability of contrast agents, procedural challenges, particularly during preparation of the patient and the contrast materials, and cost are disadvantages associated with known contrast media used sonographically.

Although conventional contrast agents function adequately, the disadvantages inherent in the conventional agents create a need for better contrast agents. One disadvantage with currently used contrast agents is that they are very expensive and difficult for some physicians to obtain. Another disadvantage is that conventional contrast agents must be shaken prior to injection to either mix the components or to generate bubbles, thus making the entire diagnostic procedure cumbersome and possibly somewhat subjective. A third disadvantage is that the contrast agent composition has a very short shelf life due to its unstable nature once it is prepared for use in a patient.

In view of these disadvantages, other solutions have been tried. One attempt to overcome these disadvantages is a contrast medium that is made from air mixed with sterile solutions of saline. Air and saline can be used in place of conventional contrast agents in sonographic investigations, due to the ultrasound reflective properties of low density phases, i.e., gas, in liquids. Generally, microbubbles of a gas are formed in the liquid carrier.

Microbubbles in liquids have been used as contrast media previously. Microbubbles may be generated by such methods as syringe motions in a back and forth manner in combinations of air and dispersants, or ultrasonic cavitation means. It is known that such microbubbles are only stable for a short amount of time. Pre-formed microparticles using temporary or permanent polymeric films have been used to address the short stability lifespan. Pressurized systems have been used to create microbubbles in solutions. The technique involves a means of generating a focused jet of gas in order to aerate the fluids with microbubbles. Such microbubbules may coalesce if there is a lag time between generation and application into the structure to be visualized, thus these methods have used a high velocity flow of liquid. Thus, limitations to this method are that the microbubbles introduced into a fluid may coalesce into a few large bubbles or one large air pocket, the microbubbles formed must be stable long enough for visualization to occur, and due to the instability of the microbubbles, it is difficult to create reproducible conditions for comparative visualizations.

Accordingly, devices and methods are needed for creating contrast agents that resolve the issues currently encountered. Particularly, methods and devices are needed for visualization of organ structure and function, such as visualization of the uterus and Fallopian tubes.

SUMMARY

The present invention comprises methods and devices for making and using contrast agents. Methods of the present invention comprise use of a device for generating a contrast agent that is used for sonographically observing organs or bodily structures, for example, the uterus and Fallopian tubes. The contrast agent device may comprise a container assembly and optionally, a catheter assembly fluidly coupled to the container assembly. A container assembly may comprise a first container for providing a solution of a liquid, such as saline, and a second container for providing a gas, such as air, and elements for creating an alternating pattern of gas and fluid, which is delivered directly to the organ or structure by the catheter assembly. A container assembly may comprise one or more containers. A container assembly may comprise elements for providing the contained substance from a container to the catheter.

Methods of the present invention comprise sonographically observing a location of a body, such as a uterus and its associated Fallopian tubes, using the devices disclosed herein. Methods comprise placement of a catheter delivery end in close approximation to the structure to be observed, and providing the fluid/gas mixture to the structure. For example, in a method of viewing a Fallopian tube, a delivery device comprising at least one catheter is placed within the uterus, and the at least one catheter is provided through the delivery device and is extended to the cornua of the uterus and the delivery end of the catheter is held in place, for example, by an end structure such as a balloon. Once the catheter(s) is in place, the liquid/gas mixture, the contrast medium, is provided from the contrast agent device to the catheter, and to the Fallopian tube(s). Sonographic visualization is begun, and one or both of the Fallopian tubes is examined. Depending on the delivery device used to provide the contrast agent, the Fallopian tubes may be examined simultaneously or sequentially. If visualization of the entire uterus is desired, for example, after visualization of the Fallopian tubes, the catheter(s) is withdrawn from the cornua, and retracted until the end structure of a single catheter is in place at the entrance to the uterus. The end structure, such as a balloon, is enlarged to provide a liquid seal of the uterus and the liquid/gas contrast agent is introduced into the uterus. Sonographic visualization is begun and may be continued until a sufficient amount of the liquid/gas contrast agent is within the uterus.

Bodily structures of humans or animals, or inanimate objects can be easily observed with the contrast agents of the present invention. Providing the contrast agent directly to the structure to be observed with a catheter assembly aids in maintaining the structure of the gas within the liquid of the liquid/gas mixture. The methods of the present invention aid in the reproducibility of the methods of visualization and comparative results therefrom.

DETAILED DESCRIPTION

Figure 1:
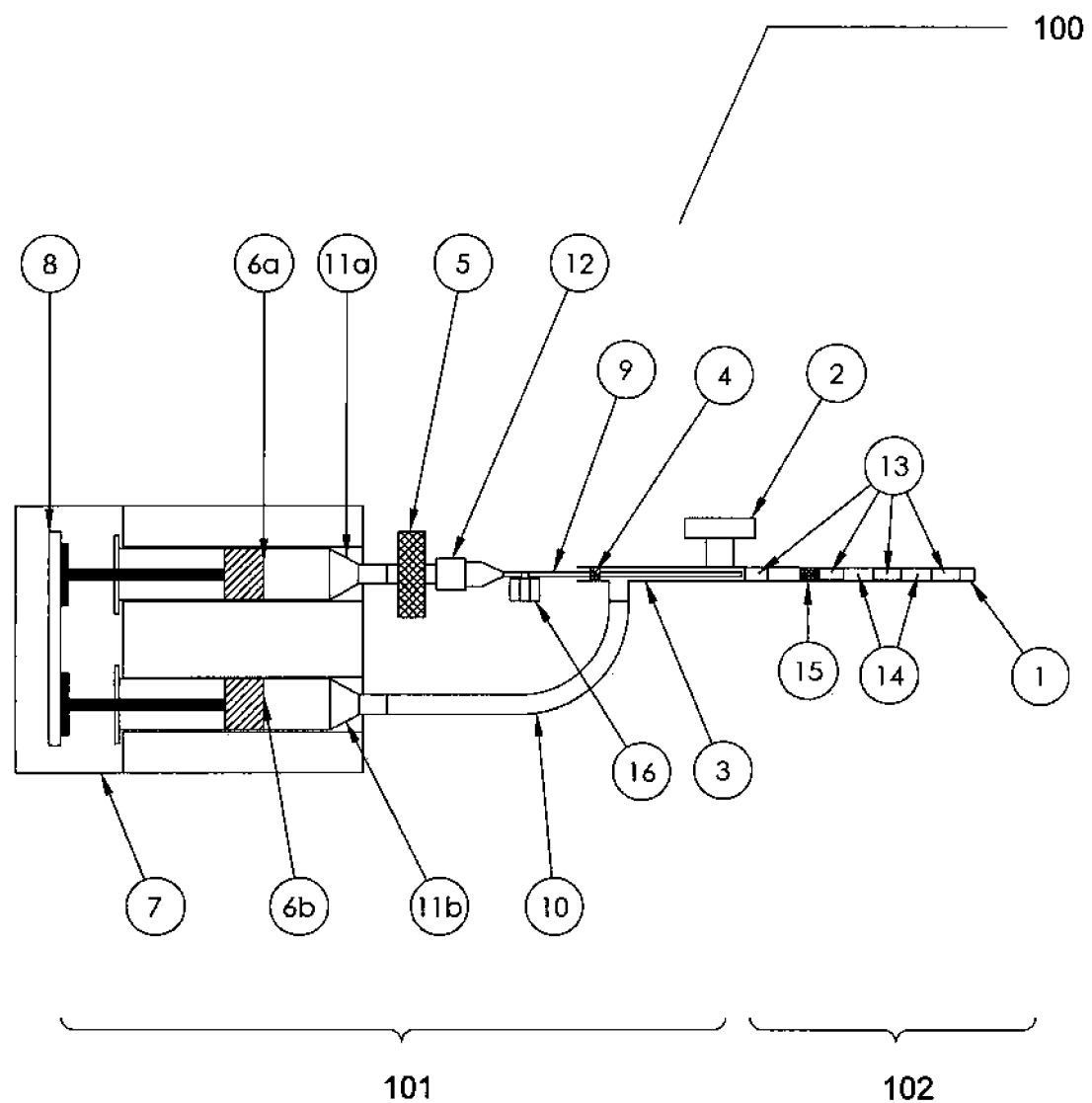
FIG. 1 is a schematic of an exemplary embodiment of the present invention.

The present invention comprises methods and devices for making and using contrast agents for ultrasound or sonography visualization of structures. Such structures may be present in the bodies of humans or animals, or may be inanimate structures. As discussed herein, the methods and devices are used for ultrasound visualization of a uterus and one or more Fallopian tubes of a mammal. It is to be understood that the methods and devices are not limited to this application, but can be used in visualization of ducts or structures, whether in living beings or inanimate structures.

The present invention comprises devices for making a contrast medium composition. As used herein, contrast agent and contrast medium mean a composition that is visible by ultrasound methods, referred to as sonography, and the terms may be used interchangeably. Methods of the present invention comprise use of a contrast agent device for generating a contrast agent that is useful for sonographically observing organs or bodily structures, for example, the uterus and Fallopian tubes.

A contrast agent device comprises a container assembly and optionally, a catheter assembly fluidly coupled to the container assembly. A container assembly may comprise at least one container for a fluid. A fluid comprises a liquid or a gas. A container assembly may comprise a first container for a liquid, such as saline, and a second container for a gas, such as air, and elements for creating an alternating pattern of gas and fluid. A container assembly may comprise elements for providing the contained fluid from a container to the catheter assembly. The container may comprise one or more outlets through which the fluid, such as gas or liquid, exits the container, or the outlet may be used to provide a fluid, either liquid or gas into the container. The container assembly may comprise a component for providing force upon the fluid contained within the container. For example, a container may be a syringe, and the component for providing force upon the fluid is a syringe plunger. The container assembly may comprise a component for activating the component for providing force. For example, the container may be a syringe, the component for providing force upon the contained fluid is a syringe plunger, and the component for activating the plunger may be a pump, or the hand of an operator.

The container assembly may further comprise fluid connections between one or more containers and a contrast pattern generating chamber. Such fluid connections include, but are not limited to, tubing or needles. The container assembly may comprise a contrast pattern generating chamber wherein the gas phase is introduced into the liquid phase and the composition exiting the contrast pattern generating chamber is characterized by alternating phases of gas and liquid which form the pattern of the contrast medium composition. The container assembly may provide the contrast medium composition to a catheter assembly or directly to a structure to be visualized.

The container assembly may be in fluid connection with the catheter assembly. The catheter assembly may be a single or double lumen catheter. The catheter may comprise end structures, such as a balloon on the delivery end of the catheter. The opposite end of the catheter, the attachment end, may have attachment elements for attaching the catheter to other elements, such as elements, such as a luer lock, to attach the catheter to a container assembly. The catheter may comprise other components such as a wire, sensors, cutting elements, retrieval elements such as clamps or pincers.

The present invention comprises devices for delivery of a contrast medium to a structure. It is contemplated by an embodiment of the present invention that the contrast medium is provided by the catheter assembly substantially directly to a structure to be visualized. In an aspect of the invention, for example, in direct delivery to a fallopian tube, the amount of contrast medium used per each fallopian tube evaluation may be small, such as less than 20 mL, less than 15 mL, less 10 mL, less than 8 mL, less than 5 mL, less than 4 mL, less than 3 mL, less than 2 mL, less than 1 mL, less than 0.5 mL. The amount of contrast fluid used may be any amount that is sufficient to provide an accurate visualization of the structure. The contrast fluid may substantially fill the structure visualized, or may only be present in particular locations within the structure.

When the structure to be visualized is a Fallopian tube, any device that provides a catheter to the Fallopian tube may be used. A catheter may be connected to the contrast media device comprising a container assembly described herein. A particular device for providing a catheter to a body structure, such as a Fallopian tube, and that is useful in methods of visualizing a Fallopian tube is the device taught in U.S. patent application Ser. No. 11/065,886, U.S. patent application Ser. No. 12/240,738, and U.S. patent application Ser.

No. 12/240,791, each of which is herein incorporated in its entirety. In general these applications disclose a device comprising a housing and an introducer shaft that is used to enter and traverse the uterus until the tip of the shaft approaches or touches the fundus of a uterus. Once the tip of the introducer shaft is at the fundus of the uterus, the device may be stabilized. One or more catheters, such as two, are fed through the introducer shaft and out into the uterine cavity. The placement of the introducer shaft allows for the three dimensional alignment of the catheter(s) with the cornua of the uterus. The catheter(s) is advanced until the delivery end(s) of the catheter(s) are in place in the cornua. An end structure, such as a balloon, is inflated or engaged, to stabilize the catheter(s) in place, and the end structure may prevent or minimize back-flow of materials exiting the catheter delivery end. Once the end structure is engaged, the catheter(s) is ready for delivery of materials or other activities.

In a method of the present invention, the catheter placed by the introducer shaft comprises the catheter assembly. The end of the catheter opposite the delivery end, referred to herein as the proximal end or the attachment end, is attached to a container assembly of a contrast medium device of the present invention. The contrast medium is generated by the actions of the container assembly and the contrast medium is provided into and through the catheter(s) and out into the cornua of the uterus and into to a Fallopian tube(s). Visualization techniques are initiated as the contrast medium enters the Fallopian tube(s) and if possible, flows through the tube(s) and out into the peritoneal cavity. If a tube is blocked, the medium will not flow. The pressure built up by the blockage may or may not unseat the balloon to relieve pressure and the flow would then be directed into the uterus.

If the device providing the catheter uses only one catheter, then visualization of one Fallopian tube occurs, followed by readjustment of the device, such as rotation of the introducer shaft, as taught in the cited patent applications, and the steps are repeated to provide a contrast medium to the other Fallopian tube. The contrast medium provided may be any currently known contrast medium that may be provided through a catheter to a location.

Methods of the present invention comprise making a contrast medium. A contrast medium device of the present invention is used to make a contrast medium. For example, a contrast medium device comprising one container for fluid may comprise a container comprising a flexible porous material contained within the container. An example wherein the container is a syringe body is described, such as one shown in FIG. 4. The present invention is not limited to this design, but contemplates other containers that would function in similar ways. The syringe is substantially filled with a flexible porous material. The flexible porous material includes, but is not limited to, strips or pieces of woven or nonwoven material, an open-celled material, such as a sponge, or fragments of a sponge, or any material that would contain a gas and release the gas when acted upon, such as by compression forces. For example, the flexible, porous material is an open-celled sponge. The sponge is placed in the container and a liquid is added, but the liquid does not displace all of the air in the sponge. The syringe plunger is applied to the large open end of the syringe and the other end of the syringe is in fluid connection with the catheter assembly. As the plunger is depressed into the syringe, the sponge is compressed and the air is forced out into the liquid, creating bubbles. The bubbles and fluid enter the catheter and transit the catheter to the structure. Visualization of the structure is then possible. See FIG. 5 for an illustration of visualization of a Fallopian tube.

The present invention comprises contrast medium devices comprising more than one container. For example, the contrast medium device may comprise two containers, such as one shown in FIG. 1, an example wherein the containers comprise a syringe body. The present invention is not limited to this design, but contemplates other containers that would function in similar ways. One of the containers, which may be a pre-filled syringe, contains a liquid. The liquid may be any of those disclosed herein, such as saline or water, or known contrast agent fluids. A second container, which may be a pre-filled syringe, contains a gas. The gas may be any of those disclosed herein, such as air, carbon dioxide, oxygen, nitrogen or halocarbon compound gases, other gases, or known contrast agent gases. The plungers of the two syringes are depressed simultaneously either manually or mechanically and the mixture of the gas and liquid form an alternating pattern of gas phase and liquid phase, which is a contrast medium. The contrast medium then enters and transits the attached catheter and exits into the structure, such as the Fallopian tube. Visualization of the structure is possible by ultrasound techniques.

Compositions of the present invention comprise a contrast medium made using the methods taught herein. A contrast medium of the present invention comprises a gas phase within a liquid carrier. The gas phase may be a bubble or may be a liquid-free, gas-filled area adjacent to a liquid phase area, and the alternating gas-filled area and liquid area may repeat multiple times. The sizes of the gas-filled areas or the liquid filled areas may be uniform in size or not. The present invention contemplates providing a contrast medium in reduced volumes, compared to amounts currently used which may be 20 mL or more, and providing the contrast medium substantially in or very near the structure to be visualized (i.e. Fallopian tube). The present invention controls the amount of gas and liquid used in combination to form the mixed gas/liquid composition, which enters the structure. The pattern of the contrast medium composition can range from predominantly a gas (air or other gas) phase to predominantly a liquid (saline or other liquid) phase and can be provided in a regular pattern or in an irregular pattern. The ratios of the gas to liquid may be determined by the size of the respective syringe. The larger the air syringe the greater the air segment in the pattern of the composition. The use of a porous structure may create a more random or irregular pattern. The amount of contrast medium delivered may be controlled by the amount of syringe plunger displacement.

A composition of the present invention may comprise a liquid and a gas, and optionally, surfactants, emulsifiers, or other stabilizing agents. The liquid, which may be seen as a carrier of the gas phase, may be any liquid that is substantially free of solids and flows at normal or bodily temperatures. For example, the liquid may be water or physiologically acceptable aqueous solutions including, but not limited to, physiological electrolyte solutions, physiological saline solutions, Ringer's solution or aqueous solutions of sodium chloride, calcium chloride, sodium bicarbonate, sodium citrate, sodium acetate, or sodium tartrate, glucose solutions, or solutions or mono- or polyhydric alcohol, e.g., ethanol, n-butanol, ethylene glycol, polyvinylpyrrolidone, or mixtures or combinations of these. Further, the liquid carrier may comprise physiologically acceptable non-aqueous solutions, including, but not limited to, anhydrous or substantially anhydrous carrier liquids, alcohols, glycols, polyglycols, synthetic perfluoranated hydrocarbons, or in mixtures or combination with other non-aqueous or aqueous liquids.

The contrast media compositions of the present invention may comprise surfactants or compounds that stabilize the gas-liquid interface. Surfactant composition may be useful when the contrast medium is provided to a structure that is larger than the catheter size used to transmit the contrast medium. Surfactants include tensides, such as lecithins; esters and ethers of fatty acids and fatty alcohols with polyoxyethylene and polyoxyethylated polyols like sorbitol, glycols and glycerol, cholesterol; and polyoxy-ethylene-polyoxypropylene polymers, viscosity raising and stabilizing compounds, mono- and polysaccharides (glucose, lactose, sucrose, dextran, sorbitol); polyols, e.g., glycerol, polyglycols; and polypeptides like proteins, gelatin, oxypolygelatin, plasma protein, amphipathic compounds capable of forming stable films in the presence of water and gases, such as the lecithins (phosphatidyl-choline) and other phospholipids, inter alia phosphatidic acid (PA), phosphatidylinositol, phosphatidylethanolamine (PE), phosphatidylserine (PS), phosphatidylglycerol (PG), cardiolipin (CL), sphingomyelins, the plasmogens, the cerebrosides, natural lecithins, such as egg lecithin or soya bean lecithin, or synthetic lecithins such as saturated synthetic lecithins, for example, dimyristoylphosphatidylcholine, dipalmitoylphosphatidylcholine or distearoylphosphatidylcholine or unsaturated synthetic lecithins, such as dioleylphosphatidylcholine or dilinoleylphosphatidylcholine, free fatty acids, esters of fatty acids with polyoxyalkylene compounds like polyoxypropylene glycol and polyoxyalkylene glycol; ethers of fatty alcohols with polyoxyalkylene glycols; esters of fatty acids with polyoxyalklated sorbitan; soaps; glycerol-polyalkylene stearate; glycerolpolyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono- di and triglycerides of saturated or unsaturated fatty acids; glycerides of soya-oil and sucrose, block copolymers of polyoxypropylene and polyoxyethylene (poloxamers), polyoxyethylenesorbitans, sorbitol, glycerol-polyalkylene stearate, glycerolpolyoxyethylene ricinoleate, homo- and copolymers of polyalkylene glycols, soybean-oil as well as hydrogenated derivatives, ethers and esters of sucrose or other carbohydrates with fatty acids, fatty alcohols, glycerides of soya-oil, dextran, sucrose and carbohydrates. Surfactants may be film forming and non-film forming and may include polymerizable amphiphilic compounds of the type of linoleyl-lecithins or polyethylene dodecanoate, phosphatidic acid, phosphatidylcholine, phosphatidylethanolamine, phosphatidylserine, phosphatidylglycerol, phosphatidylinositol, cardiolipin, sphingomyelin and biocompatible and amphipathic compound capable of forming stable films in the presence of an aqueous phase and a gas, phospholipids including phosphatidylcholine (PC) with both saturated and unsaturated lipids; including phosphatidylcholine such as dioleylphosphatidylcholine; dimyristoylphosphatidylcholine (DMPC), dipentadecanoylphosphatidylcholine-, dilauroylphosphatidylcholine (DLPC); dipalmitoylphosphatidyl-choline (DPPC); disteraoylphosphatidylcholine (DSPC); and diarachidonylphosphatid-ylcholine (DAPC); phosphatidylethanolamines (PE), such as dioleylphosphatidylethanolamine, dipaimitoylphosphatidylethanolamine (DPPE) and distearoylphosphatidylethanolamine (D SPE); phosphatidylserine (PS) such as dipalmitoyl phosphatidylserine (DPPS), disteraoylphosphatidylserine (DSPS); phosphatidylglycerols (PG), such as dipalmitoylphosphatidylglycerol (DPPG), distearoylphosphatidylglycerol (DSPG); and phosphatidylinositol.

The contrast medium compositions comprise gases, and any physiologically acceptable gas may be present in the compositions of the present invention. The term "gas" as used herein includes any substances (including mixtures) substantially in gaseous form at the normal human body (37° C.). Close to 200 different gases have been identified as potentially useful for making ultrasound contrast agents, and include oxygen, air, nitrogen, carbon dioxide or mixtures thereof, helium, argon, xenon, krypton, $CHClF_2$ or nitrous oxide, sulfur hexafluoride, tetrafluoromethane, chlorotrifluoromethane, dichlorodifluoro-methane, bromotrifluoromethane, bromochlorodifluoromethane, dibromo-difluoromethane dichlorotetrafluoroethane, chloropentafluoroethane, hexafluoroethane, hexafluoropropylene, octafluoropropane, hexafluoro-butadiene, octafluoro-2-butene, octafluorocyclobutane, decafluorobutane, perfluorocyclopentane, dodecafluoropentane, fluorinated gases including materials which contain at least one fluorine atom such as $SF_6$, freons (organic compounds containing one or more carbon atoms and fluorine, i.e. $CF_4$, $C_2F_6$, $C_3F_8$, $C_4F_8$, $C_4F_{10}$, $CBrF_3$, $CCl_2F_2$, $C_2ClF_5$ and $CBrClF_2$ and perfluorocarbons. The term perfluorocarbon refers to compounds containing only carbon and fluorine atoms and includes saturated, unsaturated, and cyclic perfluorocarbons such as perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes and perfluoroheptanes; perfluoroalkenes such as perfluoropropene, perfluorobutenes (e.g. perfluorobut-2ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane.). The saturated perfluorocarbons, which are usually preferred, have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$ $C_4F_8$, $C_4F_{10}$, $C_5F_{12}$, $C_6F_{12}$, $C_7F_{14}$, $C_8F_{18}$, and $C_9F_{20}$.

The present invention comprises embodiments of a contrast medium device. A device may be two separable components; a container assembly and a catheter assembly that locates the fluid output of the catheter assembly near or in the targeted duct or cavity. Alternatively, a contrast medium device may be of a single, one-piece construction with a container assembly adjoined to a catheter assembly. A contrast medium device may comprise a container assembly, and optionally, a catheter assembly. A contrast medium device may comprise a container assembly that provides a contrast medium comprising a gas phase and a liquid phase. The contrast medium device may comprise a container assembly comprising a modified conventional multiple syringe pump, either a mechanical or a manual handheld device capable of accepting variously sized syringes. The syringe outputs are directed into a mixing chamber or conduit where the appropriately created train of gas (i.e. air) and liquid (i.e. saline) are then driven into the input of a catheter assembly. Directed delivery of the injected contrast media in the proximity or within the duct (i.e. Fallopian tube) will allow for sonography of the structure. The contrast medium composition is provided directly to the fallopian tube, by which is meant that the contrast medium composition is delivered only to the fallopian tube, or only to the fallopian tube first, and not by a filling of the uterus with a fluid and having that fluid overflow into the fallopian tubes. Providing a composition directly to a structure is meant herein to mean that the composition is provided at or near an opening of the structure to be assessed, so that the composition enters the structure and does not flow into the structure from a remote site of delivery of a composition.

An aspect of the present invention comprises a contrast medium device comprising a container assembly comprising a contrast pattern generating chamber having a diameter in a range of 0.3 to 1.8 ratio to the diameter of the structure to be visualized. The diameter of the contrast pattern generating chamber may be in a ratio of 0.1 to 100 the diameter of the structure to be visualized. The contrast pattern generating chamber may have a diameter ratio of 0.5 to 1 of the structure to be visualized, a diameter ratio of 1 to 1 of the structure to be visualized, a diameter ratio of 1 to 1.5 of the structure to be visualized, a diameter ratio of 1 to 2 of the structure to be visualized. An aspect of a contrast medium device comprises a container assembly comprising a contrast pattern generating chamber that has a diameter substantially equal to the diameter of the structure to be visualized, wherein the ratio of the diameters is 1.

The interfaces of the alternating gas and liquid phases must be present in sufficient numbers if a duct, tube or structure is to be visualized by this contrast medium, and both phases must be present in the viewing region during the time of viewing. It is the presence of both phases traversing the viewing region that provide the visualization contrast. For example, if only one phase (either liquid or gas) is visible in the viewing region at a given time, assessment difficult or impossible. By the creation of multiple interfaces between the two phases in the contrast medium, observation of structure is possible due to the flow of the contrast medium comprising the interfaces of the phases.

An aspect of the present invention comprises contrast medium devices comprising contrast pattern generating chambers having diameters similar in diameter to the structure being observed. For example, if gas phase is created that is smaller than the diameter of the structure to be observed, the gas will rise to the upper portion of the duct and coalesce with another gas phase and fill the diameter of the structure. An aspect of the present invention comprises contrast medium devices comprising contrast pattern generating chambers having diameters that are either larger or smaller in diameter to the structure being observed. For example, if very small gas phases are created in the contrast pattern generating chamber, the small gas phases can be maintained in a larger diameter structure using dispersing agents, surfactants, or other similar acting components in the liquid or gas phase. Such small gas phases may be achieved by vibratory manipulation of the container assembly. The higher the frequency of the oscillations, the smaller the released gas phase bubbles.

A manual means of creating a contrast medium can be achieved by the use of a contrast medium device comprising a container assembly comprising a single syringe and a porous substance, such as open cell foams, sponges, or woven or non-woven fabrics or fibers or combinations thereof. The syringe is charged with one or more of these substances in a loosely fitted fashion and the plunger is then replaced in the fully retracted position. The contrast medium is then injected or otherwise fed or drawn into the syringe chamber containing the porous substance(s). Upon controlled depression of the syringe plunger, the fluid and air or other gas egresses in a manner similar to the dual syringe system described above. The catheter assembly delivers the contrast medium into the structure being assessed.

A use of the devices disclosed herein is to deliver compositions to a structure to be visualized. Diagnostic or therapeutic treatments may be provided to humans or animals by delivering diagnostic compositions, such as contrast medium compositions, or therapeutic compositions comprising therapeutic agents to a structure by using the contrast medium device and a catheter assembly as described herein. For example, therapeutic compositions may be provided to a Fallopian tube in combination with alternating phase interfaces provided by the introduction of a gas to the composition, and for treatment of the Fallopian tube may comprise methotrexate, hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, other compounds that may treat or prevent conditions related to the fallopian tube, uterus, ovaries, or other organs or coverings reached by a composition flowing from the cornua or ostia of a fallopian tube or combinations thereof. Therapeutic compositions comprise hormones for fertility, fertility enhancing compounds, gametes, sperm, ova, combinations of sperm and ova, one or more zygotes, or one or more embryos, or combinations thereof. In methods where delivery of such diagnostic or therapeutic compositions are provided by directly providing such compositions to structures, the compositions may further comprise the intermingling of a gas with the diagnostic or therapeutic composition, and the delivery of the diagnostic or therapeutic compositions may be monitored by techniques such as ultrasound. A composition comprising therapeutic agents combined with the interfaces created by combining a gas with the therapeutic composition using a contrast medium device of the present invention may provide both treatment and diagnosis of the condition of a structure in one step of delivering the composition. Alternatively, the combined therapeutic agent composition with interfaces from gas/liquid phases may be employed to limit or locate the medicament in the targeted structure with the support of sonographic imaging allowing for diagnosis and treatment to occur simultaneously or in sequence.

FIG. 1 presents a schematic of an embodiment of contrast medium device 100 comprising container assembly 101, and shows a portion of a catheter assembly 102 in fluid connection with container assembly 101, for creating alternating and repetitive interfaces of gas and liquid phases. The container assembly 100 may be coupled to a catheter assembly comprising a catheter 1. The dimensions of a contrast pattern generating chamber 3 and/or a catheter may have diameters so as to maintain the distinct gas/liquid phases and thereby minimize coalescing of like phases. In some embodiments, diameters of the contrast generating chamber and the catheter may range from about 0.5 mm to about 5.0 mm. A pressure relief valve 2 may minimize undue pressure build up in a structure, such as in a Fallopian tube, if the structure is blocked, such as if a Fallopian tube is not patent. Such valves may be used in line in other locations in the device (not shown) or embodiments may have no valves. It may also function as a secondary relief to an end structure on a catheter, such as a balloon, when the catheter is positioned in the entryway to the Fallopian tube, the cornua, and the end structure acts to hold the catheter in place.

The contrast pattern generating chamber 3 creates the phases with interfaces between a liquid (e.g., saline) phase 14 and the gas (e.g., air) phase 13. Formation of interfaces between gas and liquid phases occurs as the two media enter the contrast pattern generating chamber upon being advanced by dual syringe pump 7. A rubber septum 4 permits a needle 9 to be inserted into contrast pattern generating chamber 3 with air tight sealing. A liquid phase is introduced into contrast pattern generating chamber 3 through a connection 10, which may be tubing. The gas or liquid may be provided from either container. Valves may be added in line, such as inn order to prevent possible flow along the path of least resistance, a one-way check valve 12 may be positioned posterior to needle 9. Preceding the check valve is an in-line aseptic filtration device 5 of 0.2 or so micron porosity, such filters may be used in line for either or both media. Embodiments of the present invention may comprise devices that do not include such valves or filters. Syringe 11a as well as syringe 11b may be pre-loaded with their respective medium, either liquid or gas, and placed and locked into dual syringe pump 7. The syringe pump drive block 8 advances the respective gas and liquid syringe plungers 6a and 6b in a simultaneous fashion. Junction 15 is formed between the contrast generating chamber and a catheter. Vibrator 16 is an optional element that is used to create vibrations through needle 9 to create smaller phases, such as bubbles, of the phase exiting needle 9, either gas or liquid.

An alternative embodiment comprises a dual pump where the drive block comprises two separate drivers for the two individual syringes. This permits the modification of the interface pattern, or the gas/liquid phases, to provide one phase in shorter or longer segments over the other. This could be accomplished by a slower (or faster) rate of delivery by one plunger over the other.

Needle 9 diameter may be somewhat smaller or slightly smaller than the diameter of the contrast pattern generating chamber to allow the phase delivered through needle 9 to be affected by the other phase in the contrast pattern generating chamber 3, so that the phase delivered by needle 9 is dispersed in discrete amounts. For example, surface tension of a liquid, delivered through needle 9, may cause a definite amount of liquid to detach from the needle end and form a liquid phase within the gas in the contrast pattern generating chamber. For example, the needle gauge can range from about 10 to 30.

Figure 2:
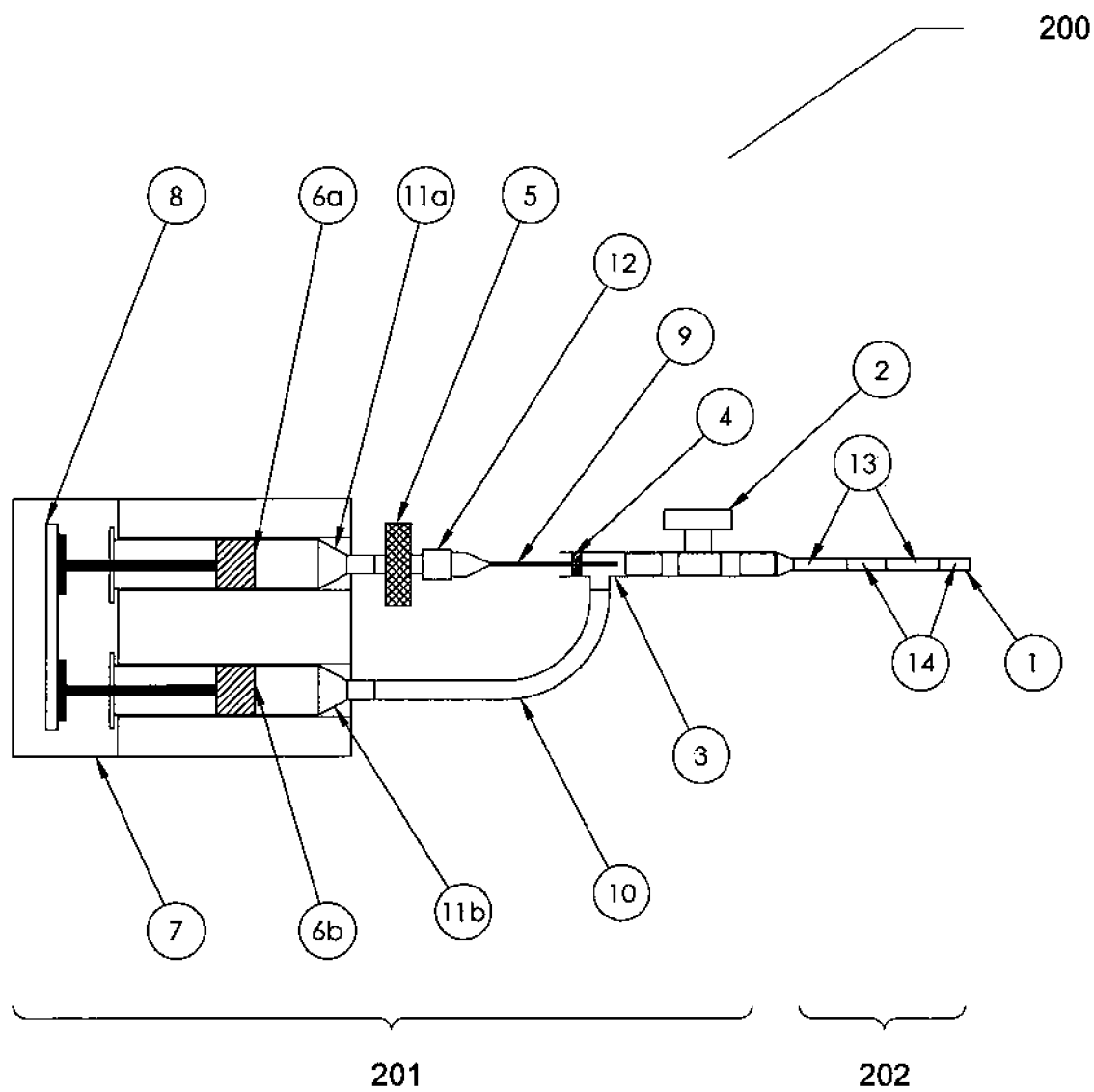
FIG. 2 is a schematic of an exemplary embodiment of the present invention.

FIG. 2 is similar to FIG. 1 except that contrast medium device 200 has a contrast pattern generating chamber having a diameter larger than a delivery catheter. FIG. 2 is numbered similarly to FIG. 1, showing container assembly 201 in fluid connection with catheter assembly 202.

Figure 3:
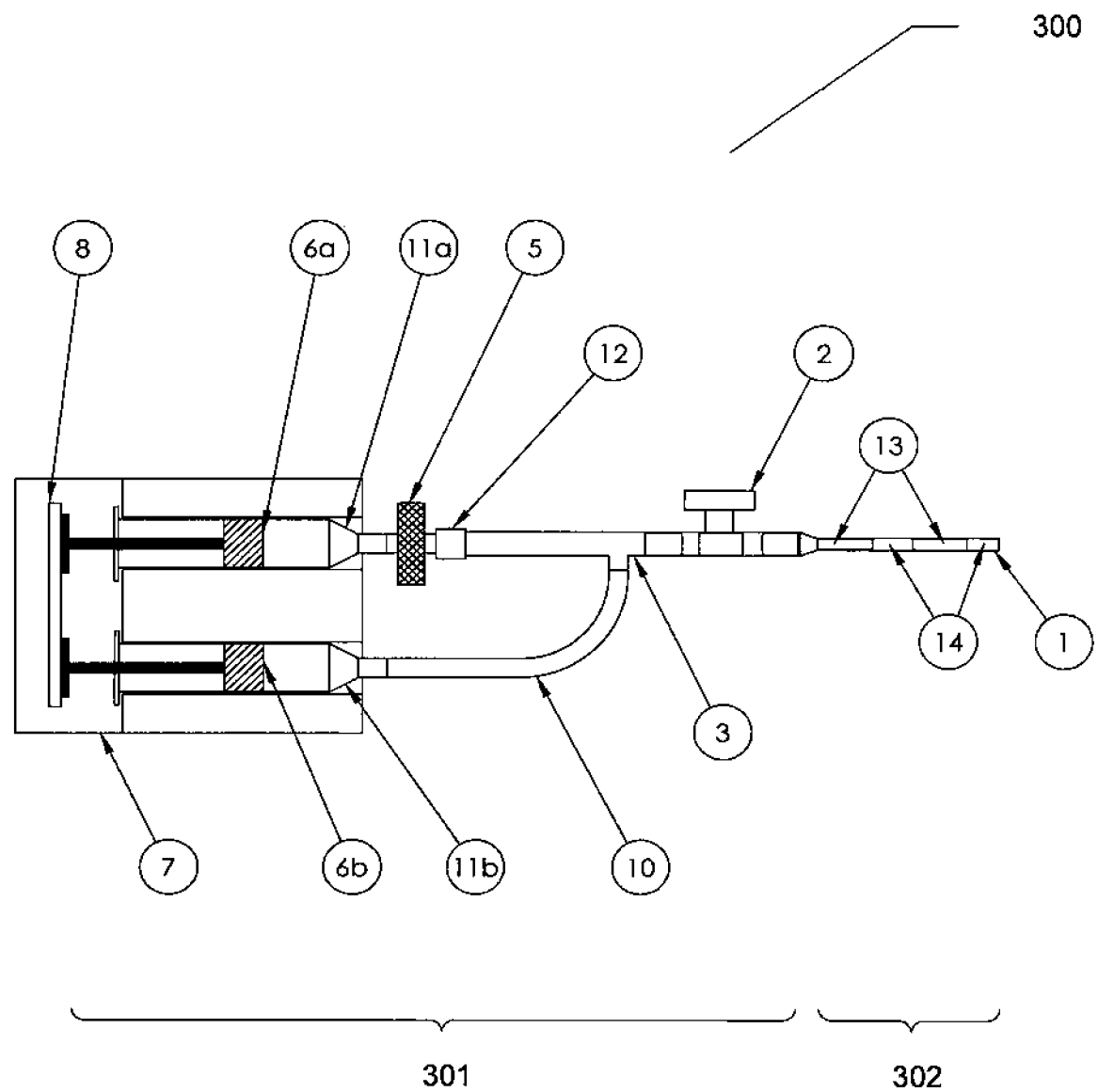
FIG. 3 is a schematic of an exemplary embodiment of the present invention

FIG. 3 is similar to FIG. 1 except that contrast medium device 300 has a contrast pattern generating chamber having a diameter larger than a delivery catheter, and no needle 9 is present. FIG. 3 is numbered similarly to FIG. 1, showing container assembly 301 in fluid connection with catheter assembly 302.

Figure 4:
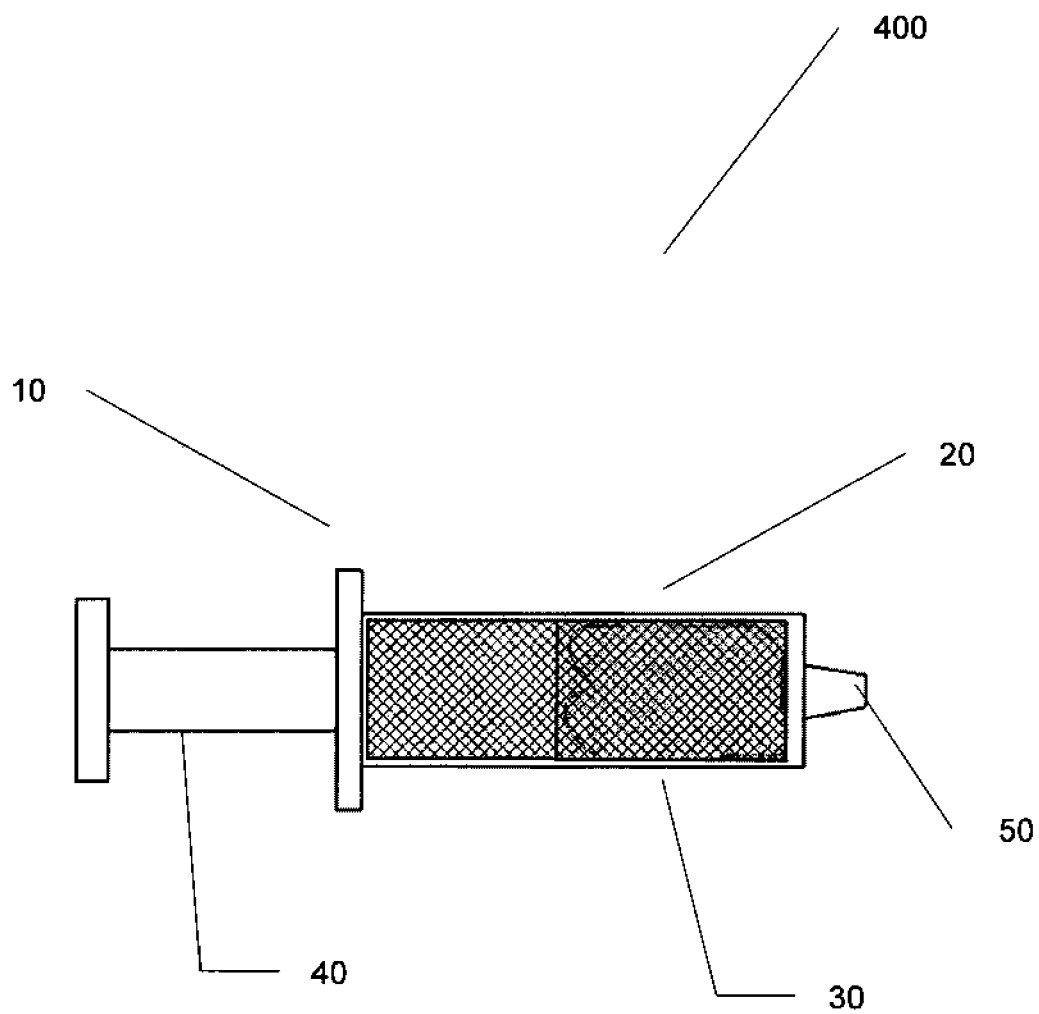
FIG. 4 is a schematic of an exemplary embodiment of the present invention.

FIG. 4 is a schematic of an embodiment of a container assembly 200 used for creating and delivering an alternating gas/liquid contrast medium to a catheter assembly or similar device. The syringe 10 is packed with a porous substance 20. The porous substance 20 is partially saturated with a liquid 30. This may be achieved by withdrawal of the plunger 40, and submersing the syringe in a liquid, injection of liquid via the syringe opening 50 or other suitable means of placement of the liquid in the interstices of the porous substance 20. For example, the porous substance may be provided in a wetted state, with the liquid already associated with the porous substance, prior to placement in the container. The syringe opening 50 is properly coupled with or without an aseptic filtration component, to a catheter assembly or similar delivery component to transfer the contrast medium to the desired site. The plunger 40 is gradually advanced so that the liquid and gas phases alternatively exit the syringe opening 50 to the catheter assembly and is delivered to the intended site to be imaged.

Figure 5:
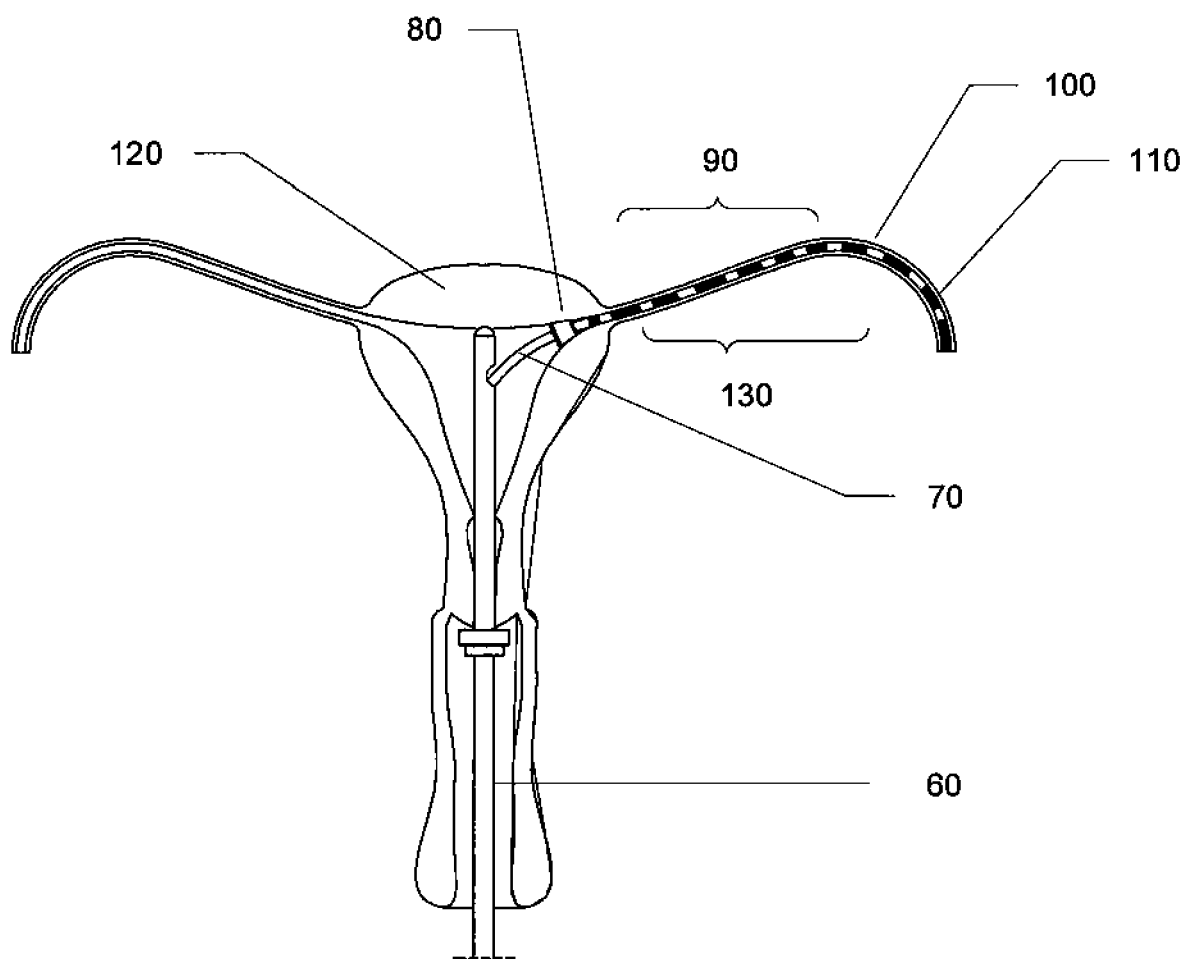
FIG. 5 is a schematic of a pattern of a contrast material in a Fallopian duct.

FIG. 5 is a schematic of visualization of a Fallopian tube using a contrast medium composition of the present invention, and a delivery device of U.S. patent application Ser. Nos. 12/240,738 and 12/240,791. Introducer shaft 60 is shown positioned in the uterus 120. The catheter assembly 70 is extended from introducer shaft 60 and delivery end of the catheter 80 is in place in the cornua of the uterus. Contrast medium 130 is present in Fallopian tube 90, and comprises contrast medium 130 with a fluid phase 100 and a gas phase 110.

Methods of the present invention comprise using a contrast medium to observe structures via ultrasound techniques. The present invention comprises making a contrast medium using liquid and gas phases in a pattern using a contrast medium device as described herein. The contrast medium is delivered directly to or in the structure to be visualized by sonography. For example, if Fallopian tubes are to be examined, the contrast medium is delivered to the uterine cornua or at the opening of the Fallopian tube by a catheter. In contrast, other known systems require filling the entire uterus with a liquid, such as saline, and then adding mixed gas/liquid composition to the saline-filled uterus and waiting until the gas/liquid mixture reaches the Fallopian tubes. Procedural limitations exist with such a method in that it requires charging the uterus with enough saline for distension before the introduction of the air and saline to visualize the Fallopian passages, the air present in the uterus or tubes may create air pockets that change fluid flow, and the patient may need to be maneuvered to odd positions for gas flow in a useful direction. The physician must perform multiple switching steps of a complex nature. The present invention may comprise a single step process which uses a simple automated contrast medium device or a handheld contrast medium devices.

With the present invention, the direct delivery of the contrast medium comprising a gas/liquid interface pattern from the contrast medium device to the Fallopian tubes will confirm patency of the tubes by the unobstructed flow during visualization and does not result in an unnecessary buildup of material in the cul-de-sac. The delivery volume may be confined to the potential volume of the Fallopian duct, approximately about 2 milliliters, for a single evaluation and may comprise a greater amount to confirm the initial observations. Imaging a Fallopian tube may comprise use of a combined fluid/gas phase composition of from about 0.5 mL to about 20 mL, from about 1 mL to about 15 mL, from about 1 mL to about 5 mL, from about 1 mL to about 10 mL, from about 10 mL to about 20 mL, from about 1 mL to about 3 mL, from about 15 mL to about 20 mL.

Tubal blockage may be evident by the lack of contrast medium mobility along the Fallopian tube into the peritoneal cavity. Ensuing pressure relief may be provided by a relief valve in the device or by movement of an end structure on the delivery catheter from its position in the cornua. A device of the present invention lends itself to being automated once the syringes have been inserted into the pumping system or activation by manual delivery once syringes are inserted into or attached to a handheld device.

An embodiment of the present invention contemplates a contrast medium delivery device that does not require supplemental systems, such as a liquid reservoirs or valve control of the fluid flow on or attached to the device. A simplified device and methods leads to a higher likelihood of a successful procedure and outcome. Further, the present device is able to maintain the pattern of alternating phases for periods of time that are useful for sonography. This permits the user the freedom to properly locate structures and reposition the patient or structure, or catheter during the procedure. Generally, there is no coalescing of individual phases. The pattern of gas/liquid phases or interfaces created by the contrast medium device is visually observed at the onset and each segment of media and rate of delivery can be controlled to suit the needs of the user.

In passageways of structures where the volumes and diameters are large, such those with diameters greater than the dimensions found in Fallopian tubes, the two phases of gas and liquid may be maintained by additives or surfactants, such as those disclosed herein. The contrast medium device may comprise larger containers than the syringes shown herein. For example, one container may be used, and the container may contain a liquid that is foamed. The foam may be created by shaking, adding foaming agents, by sonication or stirring. The foam may be transferred to the cavity to be imaged by transporting the foam from the container assembly through a catheter assembly to the structure to be assessed. It is apparent that other methods of creating the dispersion are possible and can include mechanized means to do so. The phase created by these methods permits one to regulate the sizes of the resultant foam by control of shaking or agitation as well as the types and concentrations of the dispersants.

The methods of the present invention allow for assessment of passageways, such as the Fallopian tube and uterine cavity, by ultrasound and provide a simple, safe and inexpensive outpatient method. Methods of the present invention comprise sonigraphically observing a location of a body, such as a uterus and its associated Fallopian tubes, using the devices and compositions disclosed herein.

In general, the present invention comprises methods and devices for visualizing structures, by providing contrast medium compositions to the structure and visualization techniques such as ultrasound. Visualization of the contrast medium in or around the structure provides information to the viewer and such methods and devices can be used for diagnosis and treatment of conditions related to the structure viewed. The methods and devices of the present invention are useful for diagnosis and treatment of conditions related to Fallopian tubes of humans and animals.

A contrast medium device of the present invention comprises a container assembly comprising at least one container for containing a fluid, a component for moving a fluid from the container, components for connecting the at least one container to the container assembly, and optionally comprising a catheter assembly in fluid connection with the container assembly. In embodiments of the invention, the container is a syringe and the component for moving a fluid from the container is a syringe plunger. Embodiments may further comprise a component for activating the syringe plunger, and the component is a mechanical pump or hand action. The devices may further comprise connecting elements to fluidly connect parts of the devices, valves, needles, filters, vibrators, pumps and other components.

Embodiments comprise devices where at least one container further comprises a porous substance and a gas. A porous substance may be any substance that can contain gas and liquid and release the gas and liquid easily upon compression or physical force upon the porous substance. For example, a porous substance may be a sponge, such as open cell polyurethane sponge, that may be compressible. For example, a porous substance may be material that contains a gas and a liquid is rigid, but collapses upon compression, to release the gas and liquid. A porous substance may be provided to a container in a dry state, wherein the porous substance contains gas, and a liquid may be added to the container so that the porous substance contains both a gas and a liquid. Alternatively, the porous substance may be wet, containing both liquid and gas, and thus be provided to a container. More liquid may be added to the container or not after insertion of the wetted porous substance. It is theorized that the porous substance comprises a gas within its pores and a liquid associated therewith the porous substance. The liquid and gas may be found within the pores or associated with the porous material in an easily releasable fashion, such as by surface tension, hydrogen bonding or other weak bonding associations.

The liquids provided to containers or porous substances may further comprise a surfactant, emulsifier, other stabilizing agents, or other dispersing agents. The liquids provided to containers or porous substances may further comprise liquids that are foamed. Liquids may be foamed by methods known in the art.

Embodiments of the present invention comprise contrast medium devices comprise a container assembly comprising two containers and a pattern contrast generating chamber in fluid connection with the containers. For example, the containers may be syringes, each comprising a component for moving fluid from the container that is a syringe plunger. Such embodiments may further comprising a component for activating the syringe plungers and the component is a mechanical pump or hand action. In two container devices, one container contains a gas and the other container contains a liquid. For example, where the containers are syringes, one contains a gas and the other syringe contains a liquid. In the present invention, where two or more containers are used in a device, the containers may be of the same or different size, volume, diameter, length or made from the same or different materials.

A method of the present invention comprising viewing structures using ultrasound techniques known to those skilled in the art. A method of sonographic visualization of a structure comprises, creating a contrast medium comprising alternating phases of a gas and a liquid in a contrast medium device comprising at least one container; providing the contrast medium to a catheter assembly, wherein the catheter assembly comprises a catheter delivery end positioned at or near a structure to be visualized; delivering the contrast medium directly to the structure to be visualized; and viewing the contrast medium in the structure by ultrasound. A method of sonographic visualization of a structure comprises observing a structure having a contrast medium of the present invention contained within it, or flowing through the structure. Methods of the present invention comprise making a contrast medium comprising admixing a gas and liquid in a contrast medium device such that alternating phases of gas and liquid, with visible interfaces between the phases that form a visible pattern by ultrasound, are created to form a contrast medium composition.

Any structure that is viewable using ultrasound may be viewed using the contrast medium compositions of the present invention, and contrast medium compositions made by the contrast medium devices taught herein. For example, a structure to be visualized is at least one Fallopian tube of a human or animal.

The contrast medium compositions of the present invention may be made with a liquid that is flowable and forms a discrete liquid phase when in contact with a gas. The contrast medium liquid may comprise visualizable liquids or not.

The contrast medium composition may further comprise a therapeutic composition. Therapeutic compositions comprise therapeutic agents including, but not limited to, methotrexate, hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, other compounds that may treat or prevent conditions related to the fallopian tube, uterus, ovaries, or other organs or coverings reached by a composition flowing from the cornua or ostia of a fallopian tube or any combination thereof, or combinations thereof. Treatment compositions comprise hormones for fertility, fertility enhancing compounds, gametes, sperm, ova, combinations of sperm and ova, one or more zygotes, or one or more embryos, or combinations thereof.

Methods of visualization of structures may comprise use of compositions made by a contrast medium device of the present invention. In embodiments, the contrast medium device comprises a container containing a porous substance and a fluid. The porous substance further comprises a gas, and the liquid may comprise a surfactant, emulsifier, other stabilizing agents, or other dispersing agents. The liquid may be foamed.

Methods of the present invention comprise delivery of a contrast medium composition of the present invention directly to the structure. For example, a contrast medium composition may be delivered directly to a Fallopian tube. The composition may be delivered by a catheter and the catheter may be provided to the location by devices known in the art and by those taught herein. For example, the catheter may be provided so that the catheter delivery end is positioned in the cornua of a uterus. The contrast medium composition is provided through the catheter and out into the opening of the Fallopian tube, and the composition flows through the Fallopian tube, if possible. The contrast medium composition is visible by ultrasound and the condition of the Fallopian tube can be determined by the visualization, diagnoses may be provided or treatment to the Fallopian tube or other structures may be provided. For example, the patency or occlusion of at least one Fallopian tube is determined when viewing the at least one Fallopian tube by ultrasound. Methods of the present invention comprise using small amounts of contrast medium composition to assess or treat structures, such as a Fallopian tube, and the amount of contrast medium to be provided to the structure is less than 20 mL for a single evaluation.

It must be noted that, as used in this specification and the appended claims, the singular forms "a," "an," and "the" include plural referents unless the context clearly dictates otherwise.

All patents, patent applications and references included herein are specifically incorporated by reference in their entireties.

It should be understood, of course, that the foregoing relates only to preferred embodiments of the present invention and that numerous modifications or alterations may be made therein without departing from the spirit and the scope of the invention as set forth in this disclosure.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Contrast Medium with Dual Syringe Pump

A container assembly comprising a dual pump was made, as generally depicted in FIG. 1, with two syringes, one 6 cc and the other 20 cc in volume. The 6 cc syringe was completely filled with saline and the 20 cc was filled with air. Sterile 0.2 µm filters (Sartorius Minisart or Whatman Syrfil-MF) were attached to the syringes, as sterile technique was desired. A 27 gauge, 3.5" length spinal needle was used to inject a gas phase into a fluid phase in the contrast pattern generating chamber to create the alternating air and liquid phase interfaces. A PICC-Nate catheter T-port extension and two lengths of extension tubing were utilized in the set-up.

Variations of syringe ID, pump volume, pump rate and pump delay settings were evaluated and yielded an acceptable contrast medium, as visualized in a catheter assembly forward of the container assembly. The contrast medium was delivered into clear PVC tubing that simulated the dimensions of a Fallopian tube. The user could alter the pattern created with the gas and liquid phases by allowing for increased volumes of gas or liquid and the speed by which the contrast medium was delivered by adjusting the settings on the pump. A fairly regular pattern of gas/liquid phase interfaces was created by the contrast medium device.

Example 2

Preparation of Contrast Medium with Handheld Dual Syringes

The assembly of Example 1 was followed using a housing to support the dual syringes. A block was placed behind the plunger of the 6 cc syringe containing saline to align with the plunger distance of the 20 cc syringe containing air. The creation of the contrast medium and its delivery to a catheter were controlled and manipulated by hand force on the plungers of the dual syringes as necessary to deliver the contrast medium into the catheter. When the two plungers of the syringes were pushed simultaneously, the pattern of the contrast medium was uniform, with substantially equal amounts of air and saline phases, alternating in the catheter. When one plunger was pushed, followed by pushing of the plunger of the other syringe, the pattern was sometimes regular and sometimes irregular, depending on the activation of the individual plungers. Although the sizes of the individual segments of air and saline phases were not uniform, the phases of liquid/air were repeated sufficiently to view easily. The contrast medium was delivered into clear PVC tubing that simulated the dimensions of the Fallopian tube.

Example 3

Preparation of Contrast Medium with Syringe Containing Porous Substance

A sterile Optipore scrubbing sponge was cut lengthwise in two equal parts. The plunger from a 60 cc syringe was removed and the sponge halves were inserted, one behind the other. The plunger was reinserted in the syringe and depressed to the 15 cc mark. The syringe tip was submerged into a sterile container of saline and the plunger was withdrawn to the 30 cc mark. The container assembly was now assembled and loaded. The container assembly was attached to a catheter assembly and the plunger was depressed to create an air and saline composition, a contrast medium composition, for sonographic visualization. The contrast medium was delivered into clear PVC tubing that simulated the dimensions of the Fallopian tube. An irregular pattern or random pattern was visualized as the user controled the delivery of the contrast medium. Although the sizes of the individual segments of air and saline phases were not uniform, the phases of liquid/air were repeated sufficiently to view easily.

Example 4

Study of Contrast Medium Created by Dual Syringe Pump in Simulated Model

A contrast medium device of FIG. 1 and Example 1 was used to deliver contrast medium created by the device, made with saline as the liquid phase and air as the gas phase, to a channel sized to mimic the human Fallopian tubes in an ultrasound phantom model (purchased from Blue Phantom, a division of Advanced Medical Technologies, LLC, Kirkland, Wash.). The delivery end of a catheter assembly was positioned in the simulated Fallopian tube. The contrast medium device pump was activated, creating the contrast medium, and the contrast medium was delivered to the model Fallopian tube and resembled the pattern shown in FIG. 5. An ultrasound machine (manufactured by GE Medical Systems, model: Voluson 730Pro) was used to visualize the contrast medium created, which traveled in real-time down the channel or simulated Fallopian tube and the gas/liquid phase contrast was visualized with the ultrasound probe.

Example 5

Study of Contrast Medium Created by Dual Syringe Pump in Human Subjects

A contrast medium device of FIG. 1 and Example 1 was used to deliver contrast medium to human subjects' fallopian tubes. The contrast medium composition was created by the device using saline as the liquid phase and air as the gas phase, each traveling through an aseptic filter of approximately 0.2 microns in size to ensure sterility. The catheter assembly was provided to the human patients using a delivery system, described in U.S. patent application Ser. No. 11/065,886 placed at the cornua of each subject. The contrast medium was delivered through the catheter of the delivery system and was visualized using an ultrasound instrument (manufacturer: GE Medical Systems, Model: Logic 500). Tubal patency was evidenced by contrast medium traversing the Fallopian tubes and exiting into the peritoneal cavity. This evaluation was conducted in real-time with assessment of contrast medium flow evident upon proper positioning of the delivery system.

Example 6

Study of Contrast Medium Created by Syringe Containing Porous Substance in Simulated Model A contrast medium device like that shown in FIG. 4 and Example 3 was used to deliver contrast medium created by the device, wherein saline was the liquid phase and air was the gas phase, to a channel sized to mimic the human Fallopian tubes in an ultrasound phantom model (purchased from Blue Phantom, a division of Advanced Medical Technologies, LLC, Kirkland, Wash.).

The porous substance used was a highly porous polyurethane open cell foam designed for protective packaging material. A delivery end of a catheter assembly was positioned in the simulated Fallopian tube and the contrast medium device was activated by hand, creating a contrast medium that was more irregular in pattern than that shown in FIG. 5. An ultrasound machine (manufactured by GE Medical Systems, model: Voluson 730Pro) was used to visualize the contrast medium created, which traveled in real-time down the channel or simulated Fallopian tube and the gas/liquid phase contrast medium composition was visualized with the ultrasound probe.

Example 7

Study of Contrast Medium Created by Syringe Containing Porous Substance in Human Subjects A contrast medium device like that shown in FIG. 4 and Example 3 was used to deliver contrast medium created by the device wherein saline was the liquid phase and air was the gas phase, to human subjects' Fallopian tubes by way of a catheter assembly incorporated in a delivery system as described in U.S. patent application Ser. No. 11/065,886. The delivery device was placed in the uterus of a human subject and the delivery end of one or both catheters were in place in the cornua of the uterus. A 60 cc sterile syringe was packed with a 3×2" sterile Optipore wound cleansing sponge (manufactured for ConvaTec, division of E.R. Squibb & Sons, LLC, Princeton, N.J.). The sponge was constructed of polyurethane and was highly porous in nature. Saline was drawn into the syringe so as to fill the syringe, but not to remove the air trapped in the sponge. The syringe was attached to the attachment end of one or both catheters of the delivery device. When the plunger of the syringe was depressed, the contrast medium was formed and was delivered through the catheter assembly, and out into the Fallopian tube(s). The contrast medium was visible under ultrasound (manufacturer: Philips, Model: HD3) This evaluation was conducted in real-time with assessment of contrast medium flow evident upon proper positioning of the delivery system.

What is claimed is:

1. A liquid and gas contrast medium-forming device, comprising a container assembly comprising two containers having the same volume, a first container for containing a gas and a second container for containing a liquid, two plungers, each disposed in a respective container, each for moving a liquid or gas from the respective container; a connection between the two plungers wherein the two plungers are connected so that the liquid and gas from the respective containers are moved simultaneously, components fluid connections for connecting each of the two containers to a contrast pattern generating chamber, wherein the gas and liquid form a gas-liquid composition having a multiply repeating pattern of discrete, alternating pattern of a gas phase and a liquid phase, and optionally comprising a catheter assembly in fluid connection with the container assembly.

2. The device of claim 1, further comprising a pump drive attached to the connection between the two plungers or to each of the two plungers in a simultaneous fashion.

3. The device of claim 1, wherein the fluid further comprises one or more of a surfactant, emulsifier, stabilizing or dispersing agents.

4. The device of claim 1, wherein at least one container is prefilled.

5. The device of claim 1, wherein both containers are prefilled.

6. The device of claim 1, wherein the gas-liquid contrast medium composition further comprises a therapeutic agent.

7. The device of claim 1, wherein the gas comprises air, carbon dioxide, oxygen, nitrogen, halocarbon compound gases, or a known contrast agent gas.

8. The device of claim 1, wherein the gas-liquid composition further comprises one or more of a surfactant, emulsifier, stabilizing or dispersing agent.

9. A method of sonographic visualization of a structure, comprising a) providing a gas-liquid contrast medium composition made by the structure of claim 1 to a catheter assembly comprising a catheter delivery end positioned at or near a structure to be visualized;

b) delivering the gas-liquid contrast medium composition to the structure to be visualized;

c) viewing the structure by sonography.

10. The method of claim 9, wherein the structure visualized is one or two fallopian tubes.

11. The method of claim 9, wherein the structure visualized is a mammalian uterus.

12. The method of claim 9, wherein the device further comprises a pump drive attached to the connection between the two plungers or to each of the two plungers in a simultaneous fashion.

13. The method of claim 9, wherein the fluid further comprises one or more of a surfactant, emulsifier, stabilizing or dispersing agents.

14. The method of claim 9, wherein at least one container is prefilled.

15. The method of claim 9, wherein both containers are prefilled.

16. The method of claim 9, wherein the gas-liquid contrast medium composition further comprises a therapeutic agent.

17. The method of claim 9, wherein the gas comprises air, carbon dioxide, oxygen, nitrogen, halocarbon compound gases, or a known contrast agent gas.

18. The method of claim 9, wherein the gas-liquid composition further comprises one or more of a surfactant, emulsifier, stabilizing or dispersing agent.

* * * * *